(12) United States Patent
Warren et al.

(10) Patent No.: US 7,368,429 B2
(45) Date of Patent: May 6, 2008

(54) PEPTIDE SPECIFICITY OF ANTI-MYELIN BASIC PROTEIN AND THE ADMINISTRATION OF MYELIN BASIC PROTEIN PEPTIDES TO MULTIPLE SCLEROSIS PATIENTS

(75) Inventors: Kenneth G. Warren, Edmonton (CA); Ingrid Catz, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 0 days.

(21) Appl. No.: 11/119,554

(22) Filed: May 2, 2005

(65) Prior Publication Data

US 2005/0209156 A1   Sep. 22, 2005

Related U.S. Application Data

(63) Continuation of application No. 09/813,463, filed on Mar. 20, 2001, now Pat. No. 7,090,982, which is a continuation of application No. 09/055,263, filed on Apr. 6, 1998, now Pat. No. 6,252,040, which is a continuation of application No. 09/007,520, filed on Jan. 15, 1998, now Pat. No. 6,258,781, which is a continuation of application No. 08/327,357, filed on Oct. 21, 1994, now Pat. No. 5,817,629, which is a continuation of application No. 07/798,099, filed on Nov. 27, 1991, now abandoned.

(30) Foreign Application Priority Data

Oct. 22, 1991   (CA)   .................................... 2053799

(51) Int. Cl.
*A61K 38/08* (2006.01)
*A61K 38/10* (2006.01)
*A61K 38/16* (2006.01)

(52) U.S. Cl. ............................ 514/12; 514/14; 514/16; 514/15; 514/13

(58) Field of Classification Search .................... None
See application file for complete search history.

(56) References Cited

U.S. PATENT DOCUMENTS

| | | | |
|---|---|---|---|
| 3,864,481 A | 2/1975 | Hashim | |
| 4,113,858 A | 9/1978 | Hashim | |
| 4,230,696 A | 10/1980 | Hashim | |
| 5,571,499 A | 11/1996 | Hafler et al. | ................... 414/43 |
| 5,571,500 A | 11/1996 | Hafler et al. | ................... 424/43 |
| 5,641,474 A | 6/1997 | Hafler et al. | ................... 424/43 |
| 5,645,820 A | 7/1997 | Hafler et al. | ................... 424/41 |
| 5,817,629 A * | 10/1998 | Warren et al. | ................. 514/13 |
| 5,858,364 A | 1/1999 | Weiner et al. | ........... 424/184.1 |
| 5,858,980 A | 1/1999 | Weiner et al. | ................. 514/13 |
| 5,869,054 A | 2/1999 | Weiner et al. | ........... 424/184.1 |
| 5,935,577 A | 8/1999 | Weiner et al. | ........... 424/184.1 |
| 5,948,764 A | 9/1999 | Gaur et al. | ..................... 514/14 |
| 6,036,957 A * | 3/2000 | Weiner et al. | ........... 424/184.1 |
| 6,039,947 A | 3/2000 | Weiner et al. | ........... 424/184.1 |
| 6,252,040 B1 * | 6/2001 | Warren et al. | ............... 530/328 |
| 7,090,982 B2 * | 8/2006 | Warren et al. | ................ 435/7.1 |

FOREIGN PATENT DOCUMENTS

| | | |
|---|---|---|
| EP | 0304279 | 2/1989 |
| EP | 0340109 | 11/1989 |
| EP | 0383620 | 8/1990 |
| WO | 80/02501 | 11/1980 |
| WO | WO 80/02501 | 11/1980 |
| WO | 88/00057 | 1/1988 |
| WO | WO 88/00057 | 1/1988 |
| WO | 88/10120 | 12/1988 |

(Continued)

OTHER PUBLICATIONS

Alberts 1994. Molecular Biology of the Cell, pp. 1206-1220.*
Kamholz et al. 1986. Proc Natl Acad Sci USA 83:4962-4966.*
Groome, N., et al., "Preparation and Properties of Monoclonal Antibodies to Myelin Basic Protein and Its Peptides," Neurochem. Int., 7:309-317 (1985).
Heuby, S., et al., "Monoclonal Antibodies Reactive with Myelin Basic Protein", Molecular Immunology, 24:1359-1364 (1987).
Barry, R., et al., "Characterization of Myelin Basic Protein Catabolism Products in the Cerebrospinal Fluid from Multiple Sclerosis Stroke and Head Injury Patients," Neurochem. Int., 18:291-300 (1991).

(Continued)

*Primary Examiner*—Robert C. Hayes
*Assistant Examiner*—Daniel E Kolker
(74) *Attorney, Agent, or Firm*—Pillsbury Winthrop Shaw Pittman LLP

(57) ABSTRACT

Human myelin basic protein (h-MBP) has a molecular weight of 18.5 KD and contains 170 amino acid residues. Synthetic peptides ranging in length from about 8 to 25 residues and covering the entire length of the protein have been produced. Antibodies to h-MBP (anti-MBP) were found to be neutralized by the synthetic peptides, in vitro, which span the h-MBP from about amino acid residue 61 to about amino acid residue 106. The peptides, which cover both the amino (about residues 1 to 63) and carboxy (about residues 117 to 162) terminals of h-MBP did not neutralize purified anti-MBP. Intrathecal administratin of peptide MBP (75-95), MBP(86-95), or MBP(82-98) produced complete binding-neutralization of free (F) anti-MBP with no change in bound (B) levels. A control peptide MBP35-58 had no effect on F or B anti-MBP levels. Intravenous administration of MBP(75-95), MBP(86-95), or MBP(82-98) resulted in significant decline of F and B CSF anti-MBP levels. Administration of MBP synthetic peptides to MS patients either intrathecally or intravenously did not have any adverse neurological effects and systemic complications did not occur. The MBP epitope for MS anti-MBP has been localized to an area between amino acid 86 and amino acid 95.

10 Claims, 25 Drawing Sheets

FOREIGN PATENT DOCUMENTS

| WO | 91/15225 | 10/1991 |
| --- | --- | --- |
| WO | 93/08212 | 4/1993 |
| WO | 93/21222 | 10/1993 |
| WO | 95/31990 | 11/1995 |
| WO | WO 95/31990 | 11/1995 |
| WO | 96/12731 | 5/1996 |
| WO | 96/12737 * | 5/1996 |
| WO | 96/16085 | 5/1996 |
| WO | 96/16086 | 5/1996 |
| WO | 96/28470 | 9/1996 |

OTHER PUBLICATIONS

Ota, K., et al., "T-Cell Recognition of an Immunodominant Myelin Basic Protein Epitope in Multiple Sclerosis," Nature 346:183-187 (1990).

Baxevanis, C.N., et al., "Peptides of Myelin Basic Portein Stimulate T Lymphocytes from Patients with Multiple Sclerosis", J. of Neuroimmunology, 22:23-30 (1989).

Martin, R., et al., "A Myelin Basic Protein Peptide is Recognized by Cytotoxic T. Cells in the Context of Four HLA-DR Types Associated with Multiple Sclerosis," The Journal of Experimental Medicine, 173:19-24 (1991).

Eylar, E.H., et al., "Suppression and Reversal of Allergic Encephalomyelitis in Rhesus Monkeys with Basic Protein and Peptides," Neurochemical Research, 4:249-258 (1979).

Martin, R., et al., "Fine Specificity and HLA Restriction of Myelin Basic Protein Specific Cytotoxic T Cell Lines from Multiple Sclerosis Patients and Healthy Individuals," The Journal of Immunology, 145:540-548 (1990).

Chou, Y.K., et al., Response of Human T Lymphocyte Lines to Myelin Basic Protein: Association of Dominant Epitopes with HLA Class II Restriction Molecules, Journal of Neuroscience Research, 23:207-216 (1989).

Sakai, K., et al., "Prevention of Experimental Encephalomyelitis with Peptides that Block Interaction of T Cells with Major Histocompatibility Complex Proteins," Proc. Natl. Acad. Sci, USA, 86:9470-9474 (1989).

Higgins, et al., "Suppression of Experimental Autoimmune Encephalomyelitis by Oral Administratio of Myelin Basic Protein and Its Fragments," Chemical Abstracts 108(19): 514 Abstract #165933t (1988).

Warren, et al., "Neutralization of Anti-Myelin Basic Protein by Cerebrospinal Fluid of Multiple Sclerosis Patients in Clinical Remission," J. Neurol. Sci., 88:185-194 (1988).

Warren, et al., "A Correlation Between Cerebrospinal Fluid Myelin Basic Protein and anti-Myelin Basic Protein in Multiple Sclerosis Patients," Ann. Neurol., 21:183-189 (1987).

Catz, et al., Detection of Anti-Myelin Basic Protein Neutralizing Factor in the CSF of MS Patients in Remission, Recent Advances in Multiple Sclerosis Therapy, 87-90 (1989).

Tourteltette, et al., "Multiple Sclerosis: The Blood-Brain Barrier and the Measurement of de novo central nervous system IgG synthesis", Neurology 28(2):76-83 (1978).

Link, et al., Principles of Albumin and IigG Analyses in Neurological Disorders. III. Evaluation of IgG Synbthesis Withing the Central Nervous System in Multiple Sclerosis, Scand. J. Clin. Lab. Invest. 37:397-401 (1977).

Daibler, et al., "Large Scale Preparation of Myelin Basic Protein From Central Nervous Tissue of Several Mammalian Species," Preparative Biochemistry, 2(2):139-165 (1972).

Tourtellette, "On Cerebrospinal Fluid Immunoglobulin-G (IgG) Quotients in multiple Sclerosis and Other Diseases", Journal of Neurological Sciences, 10:279-304 (1970).

Warren, et al., "Cerebrospinal Fluid Antibodies to Myelin Basis Protein in Acute Idiopathic Optic Neuritis", Ann. Neurol. 23:297-299 (1988).

Vandenbark, et al., Determinnants of Human Myelin Basic Protein That Induce Encephalitogenic T Cells in Lewis Rats, The Journal of Immunology, 143(11):3512-3516 (1989).

Groome, et al., "New Monoclonal Antibodies Reactive with Defined Sequential Epitopes in Human Myelin Basic Protein," Chemical Abstracts 110(1):558 Abstract #5882p (1989).

Katz, et al., "Antigenic and Structural Characterization of Multiple Subpopulations of H3N2 Influenza Virus from an Individual," Chemical Abstracts 109(19):548 Abstract #168486f (1988).

Gilliom, et al., "Separation of Myelin Basic Protein Peptide 43-88 and its Fragments by Analytic and Preparative High-Performance Liquid Chromatography," Chemical Abstracts 98(13): 304 Abstract #103708q (1983).

Warren, et al., "Cerebrospinal Fluid Autoantibodies to Myelin Basic Protein in Multiple Sclerosis Patients," J. Neurol. Sci., 91:143-151 (1989).

Warren, et al., "A Myelin Basis Protein Antibody Cascade in Purified IgG from Cerebrospinal Fluid of Multiple Sclerosis," J. Neurol. Sci., 96:1927 (1990).

Warren, et al., "Diagnostic Value of Cerebrospinal Fluid Anti-Myelin Basic Protein in Patients with Multiple Sclerosis," Ann. Neurol., 209:20-25 (1986).

Campbell, et al, "Myelin Basic Protein Administration in Multiple Scelrosis," Arch. Neurol., 29:10-15 (1973).

Gonsette, et al., "Failure of Basic Protein Therapy for Multiple Sclerosis," J. Neurol., 216:27-31 (1977).

Romine, et al., "A Study of Myelin Basic Protein as a Therapeutic Probe in Patients with Multiple Sclerosis," *In Multiple Sclerosis*, Hallpike et al., eds., Williams and Wilkins, Baltimore, pp. 621-630 (1982).

Pantich, et al., "CSF Antibody to Myelin Basic Protein," Arch. Neurol., 37:206-209 (1980).

Catz, et al., "Intrathecal Synthesis of Autoantibodies to Myelin Basic Protein in Multiple Sclerosis," Can. J. Neurol. Sci., 13:21-24 (1986).

Groome, et al., "New Monoclonal Antibodies Reactive with Defined Sequential Epitopes in Human Myelin Basic Protein," Journal of Neuroimmunology, 19:305-315 (1988).

Hruby, et al., "Sites in Myelin Basic Protein that React with Monoclonal Antibodies", Journal of Neurochemistry, 44:2 637-650 (1985).

Price, et al., "Multiple Epitopes in a Dodecapeptide of Myelin Basic Protein Determined by Monoclonal Antibodies", The Journal of Immunology, 136(7):2426-2431 (1986).

* cited by examiner

PEPTIDE SPECIFICITY OF ANTI-MYELIN BASIC PROTEIN AND THE ADMINISTRATION OF MYELIN BASIC PROTEIN PEPTIDES TO MULTIPLE SCLEROSIS PATIENTS

RELATED APPLICATIONS

This application is a continuation application of U.S. application Ser. No. 09/813,463, filed Mar. 20, 2001 now U.S. Pat. No. 7,090,982, which is a continuation of U.S. application Ser. No. 09/055,263, filed Apr. 6, 1998, now U.S. Pat. No. 6,252,040, which is a continuation of U.S. application Ser. No. 09/007,520, filed Jan. 15, 1998, now U.S. Pat. No. 6,258,781, which is a continuation of U.S. application Ser. No. 08/327,357, filed Oct. 21, 1994, now U.S. Pat. No. 5,817,629, which is a continuation of U.S. application Ser. No. 07/798,099, filed Nov. 27, 1991 now abandoned, which claims priority to Canadian application No. 2,053,799, filed Oct. 22, 1991.

FIELD OF INVENTION

This invention is concerned with selected polypeptides and their use in the immunoregulation of antibodies to human myelin basic protein. This invention also relates to novel pharmaceutical compositions containing these selected polypeptides and to a method of using these peptides for the treatment of Multiple Sclerosis.

BACKGROUND AND PRIOR ART

Multiple sclerosis (MS) is a multifocal demyelinating disease of the human central nervous system (CNS) associated with inflammation. Increased intra-blood-brain barrier (intra-BBB) IgG synthesis is a hallmark of MS (Tourtelotte, W. W., J Neurol Sci 10: 279-304, 1970; Link, H. and Tibbling, G., Scand J Clin Lab Invest 37: 397-401, 1977; Tourtelotte, W. W. and Ma, B., Neurology 28: 76-83, 1978; Walsh, J. M. and Tourtelotte, W. W., In: Hallpike, J. F., Adams, C. W. M. and Tourtelotte, W. W., eds. Multiple sclerosis. Baltimore. Williams & Wilkins, 1982: 275-358; and Warren, K. G., and Catz, I. Ann Neurol 17: 475-480, 1985).

IgG synthesis within the BBB is generally elevated in clinically definite MS patients (Schumacher, G. A., Beebe, G., Kibler R. E., et al., Ann NY Acad Sci 15:266-272, 1965) with active or inactive disease. The specificity of the majority of the CNS IgG is unknown. While a small proportion has antiviral activity or reacts against brain antigens, nucleic acids, erythrocytes or smooth muscle antigens, the nonspecific portion may represent polyclonal activation of B-cells (Tourtelotte, W. W., and Ma, B., Neurology 28:76-83, 1978). During the last decade there has been considerable interest in the study of antibodies to specific myelin proteins.

Following the detection of circulating immune complexes containing myelin basic protein (MBP) as their antigenic component (Dasgupta, M. K., Catz, I, Warren, K. G. et al., Can J Neurol Sci 10:239-243, 1983), increased titers of antibodies to MBP (anti-MBP) were observed in the cerebrospinal fluid (CSF) of patients with active forms of MS (Warren, K. G. and Catz, I., Ann Neurol 209:20-25, 1986). Clinically, MS is characterized by phases of disease activity such as acute relapses or chronic progression, and by phases of clinical remission. Active MS is associated with increased levels of intrathecally produced anti-MBP (Warren, K. G. and Catz, I., Ann Neurol 209:20-25, 1986; and Catz, I. and Warren, K. G., Can J Neurol Sci 13:21-24, 1986). These antibodies are found predominantly in free (F) form during acute relapses and predominantly in bound (B) form when the disease is insidiously progressive (Warren, K. G. and Catz, I., Ann Neurol 209:20-25, 1986). During acute relapses, CSF anti-MBP titers correlated with disease activity (Warren, K. G. and Catz, I., Ann Neurol 21:183-187, 1987). Anti-MBP levels were also increased in patients with first attacks of optic neuritis and in most patients experiencing first attacks of MS (Warren, K. G., Catz, I., and Bauer, C., Ann Neurol 23:297-299, 1988; Warren, K. G. and Catz, I., J Neurol Sci 91:143-151, 1989).

Longitudinal kinetic studies of CSF anti-MBP levels in patients who enter the recovery phase subsequent to an acute relapse, demonstrated a gradual decline in F anti-MBP titers commensurate with a progressive rise in B fractions (Warren, K. G. and Catz, I., J Neurol Sci 91:143-151, 1989; Warren, K. G. and Catz, I., J Neurol Sci 88:185-194, 1988). In the remission phase, CSF anti-MBP may become undetectable suggesting an anti-MBP neutralization associated with inactive phases of MS (Warren, K. G. and Catz, I., J Neurol Sci 88:185-194, 1988). In contrast, chronic-progressive MS characterized by persistence of increased anti-MBP over long periods of time was associated with inhibition of anti-MBP neutralization (Warren, K. G. and Catz, I., J Neurol Sci 88:185-194, 1988). Recently a myelin basic protein antibody cascade, identified in the IgG fraction purified from CSF of MS patients, contained anti-MBP, antibodies which neutralize anti-MBP and antibodies which inhibit anti-MBP neutralization (Warren, K. G. and Catz, I., J Neurol Sci 96:19-27, 1990).

Our previous research has demonstrated from the B-cell autoimmune point of view that there are at least two distinct forms of MS with the majority of patients having autoantibodies to myelin basic protein (anti-MBP) and a lesser number having antibodies to proteolipid protein (anti-PLP) (Warren, K. G. et al., Ann. Neurol. 35, 280-289, 1994). In anti-MBP associated MS, acute relapses are associated with elevated (greater than 1) Free (F)/Bound (B) anti-MBP ratios whereas the chronic progressive phase is characterized by F/B anti-MBP ratios of equal or less than 1, and patients in remission sometimes have mildly elevated B anti-MBP titers (Warren, K. G. and Catz, I., J. Neurol. Sci. 88, 185-194, 1989).

It has been demonstrated that some of the proliferating T-cells in MS patients are directed towards MBP (Allegretta et al., Science, 247, 718-721, 1990) and that human T-cells can recognize multiple epitopes on the molecule (Richert et al., J. Neuroimmun 23, 55-66, 1989). MBP also appears to be capable of activating some T-cells without the involvement of antigen presenting cells (Altman et al., Eur. J. Immun. 17, 1635-1640, 1987). It is likely that small peptides of MBP may be recognized by T-cells without the requirement for intracellular processing, simply by their ability to bind class II major histocompatibility antigens on the surface of presenting cells.

Since experimental allergic encephalomyelitis (EAE), an accepted animal model of MS, can be induced by inoculating susceptible rodents with either MBP or PLP in conjunction with Freund's complete adjuvant, the process of MS demyelination may have an autoimmune mechanism (Fritz, R. B. et al., J. Immunol. 130, 1024-1026, 1983; Trotter, J. L. et al., J. Neurol. Sci. 79, 173-188, 1987). From B-cell autoantibody point of view, the MBP epitope targeted by the disease process has been localized proximal to the tri-ProII sequence (residues-99-100-101-) to an area between residues 80 and 100 (Warren, K. G. et al., Ann. Neurol. 35, 280-289, 1994). This B-cell epitope overlaps the immunodominant epitope for T cells reactive to MBP, which are found in MS brain lesions (Oksenberg, J. R. et al., Nature, 362, 68-70, 1993).

Previous studies have shown that anti-MBP is neutralized by MBP. However, previous attempts to treat MS by intramuscular or subcutaneous administration of heterologous MBP have not been successful (Campbell, B., Vogel, R. J., Fisher, E. and Lorenz, R., Arch Neurol 29:10-15, 1973; Gonsette, R. E., Delmotte, P. and Demonty, L., J Neurol 216:27-31, 1977; and Romine, J. S. and Salk, J., In: Hallpike, J. F., Adams, C. W. M. and Tourtelotte, W. W., eds. Multiple sclerosis. Baltimore, Williams & Wilkins, 1982: 621-630). The problem with using native MBP is two-fold. Firstly, the protein is prepared from human brain samples and accordingly there is a potential danger that latent neuroviruses may be present in the sample. Secondly, although soluble MBP is not usually an immunogen, it is possible that when administered to individuals with an altered immune system, soluble MBP could act as an antigen and cause the production of antibodies against MBP.

Accordingly, the present invention determines whether anti-MBP purified from CSF of MS patients can be neutralized by selected soluble peptides of human MBP (h-MBP). For this purpose, soluble synthetic peptides covering the entire length of h-MBP were used to determine the possible epitope range on h-MBP which neutralizes anti-MBP obtained from these patients. Therefore selected soluble peptides, which demonstrate neutralization of anti-MBP, can be used to treat MS more effectively than the whole molecule. These soluble peptides are synthetically produced and as such no potential threat of neuroviruses would exist. Additionally, due to their small size, these peptides could not act as an immunogen. Therefore, the use of selected peptides as a treatment for MS, would overcome the problems identified with using the native protein.

Further the peptides of the present invention were investigated to determine their effectiveness in binding or modulating the production of MS anti-MBP in vivo.

The kinetic curves of the 12 peptides that did not neutralize MBP fell within the striped area.

SUMMARY OF INVENTION

According to the present invention there is provided, peptides which are substantially homologous in sequence to a part of the amino acid sequence of a human myelin basic protein. These peptides are capable of neutralizing or modulating the production of anti-MBP.

According to the present invention the peptides are of the formula:

$$R_1\text{-Val-His-Phe-Phe-Lys-Asn-Ile-}R_2$$

(SEQ ID NO:2)

and salts thereof, wherein $R_1$ and $R_2$ are independently selected from the group consisting of hydrogen, hydroxy, the residue of an amino acid and the residue of a polypeptide; provided that $R_1$ and $R_2$ are not both hydrogen or hydroxyl at the same time. The peptide can contain substitutions, deletions or additions thereof, provided that the peptide maintains its function of neutralizing or modulating the production of anti-MBP.

Examples of said peptides are selected from:
(SEQ ID NOS:3 to 13)

```
MBP75-95
Lys Ser His Gly Arg Thr Gln Asp Glu Asn Pro Val
Val His Phe Phe Lys Asn Ile Val Thr

MBP64-78
Ala Arg Thr Ala His Tyr Gly Ser Leu Pro Gln Lys
Ser His Gly

MBP61-75
His His Pro Ala Arg Thr Ala His Tyr Gly Ser Leu
Pro Gln Lys

MBP69-83
Tyr Gly Ser Leu Pro Gln Lys Ser His Gly Arg Thr
Gln Asp Glu

MBP80-97
Thr Gln Asp Glu Asn Pro Val Val His Phe Phe Lys
Asn Ile Val Thr Pro Arg

MBP91-106
Lys Asn Ile Val Thr Pro Arg Thr Pro Pro Pro Ser
Gln Gly Lys Gly

MBP84-93
Asn Pro Val Val His Phe Phe Lys Asn Ile

MBP85-94
Pro Val Val His Phe Phe Lys Asn Ile Val

MBP86-95
Val Val His Phe Phe Lys Asn Ile Val Thr

MBP87-96
Val His Phe Phe Lys Asn Ile Val Thr Pro

MBP82-98
Asp Glu Asn Pro Val Val His Phe Phe Lys Asn Ile Val
Thr Pro Arg Thr
```

Further according to the present invention there is provided pharmaceutical compositions, which comprises as an active ingredient a peptide as described above, either alone or in combination, in admixture with a pharmaceutical acceptable carrier.

Further according to the present invention, there is provided a method of treating multiple sclerosis comprising administering an effective amount of a peptide as, described above, either alone or in combination to effectively neutralize or modulate the production of anti-human myelin basic protein.

cpm: counts per minute radioactivity units=cpm sample–cpm blank/cpm total–cpm blank open circles: Bound (B) anti-MBP determined after acid hydrolysis of CSF immune complexes.
closed circles: Free (F) anti-MBP FIG. 5—Control patients: CSF anti-MBP levels in 2 "time controls" (1F56, FIG. 5A and 3M66, FIG. 5B) and 2 "time-saline controls" (4M45, FIG. 5C and 5M59, FIG. 5D). In all four patients F and B anti-MBP remained constantly elevated at baseline level when CSF was sampled every 30 minutes for the first two hours as well as 24 hours later. Symbols as in FIG. 4.

FIG. 6—Interpatient peptide studies: CSF anti-MBP levels in a group of four patients (10F38, FIG. 6A; 13F43, FIG. 6C; 5M59, FIG. 6D; and 3M66, FIG. 6G) who received increasing amounts (1, 2.5, 5 and 10 mg respectively) of a non-binding, control synthetic peptide MBP35-58 and a paired group of four other MS patients (6F53, FIG. 6B; 8M41, FIG. 6D; 4M45, FIG. 6F; and 1F56, FIG. 6H) who received increasing amounts (1, 2.5, 5 and 10 mg respectively) of the anti-MBP binding synthetic peptide MBP75-95. CSF F anti-MBP was bound in a dose-dependent fashion by peptide MBP75-95 and it did not react with peptide MBP35-58. Bound anti-MBP remained virtually unaffected.

FIG. 7—Intrapatient peptide studies: when MS patients were either "time controls" (1F56, FIG. 7C and 3M66, FIG. 7D) or "time-saline controls" (5M59, FIG. 7A and 4M45, FIG. 7B), or when they received the non-binding, control peptide MBP35-58 (5M59 and 3M66) their F and B CSF anti-MBP levels remained unaffected. In contrast, when the same patients 4M45, 1F56 and 3M66 later received 5-10 mg of the anti-MBP binding peptide MBP75-95, their F anti-MBP became undetectable for periods up to 7 days and returned to baseline level between 10 and 21 days.

Figure 8:
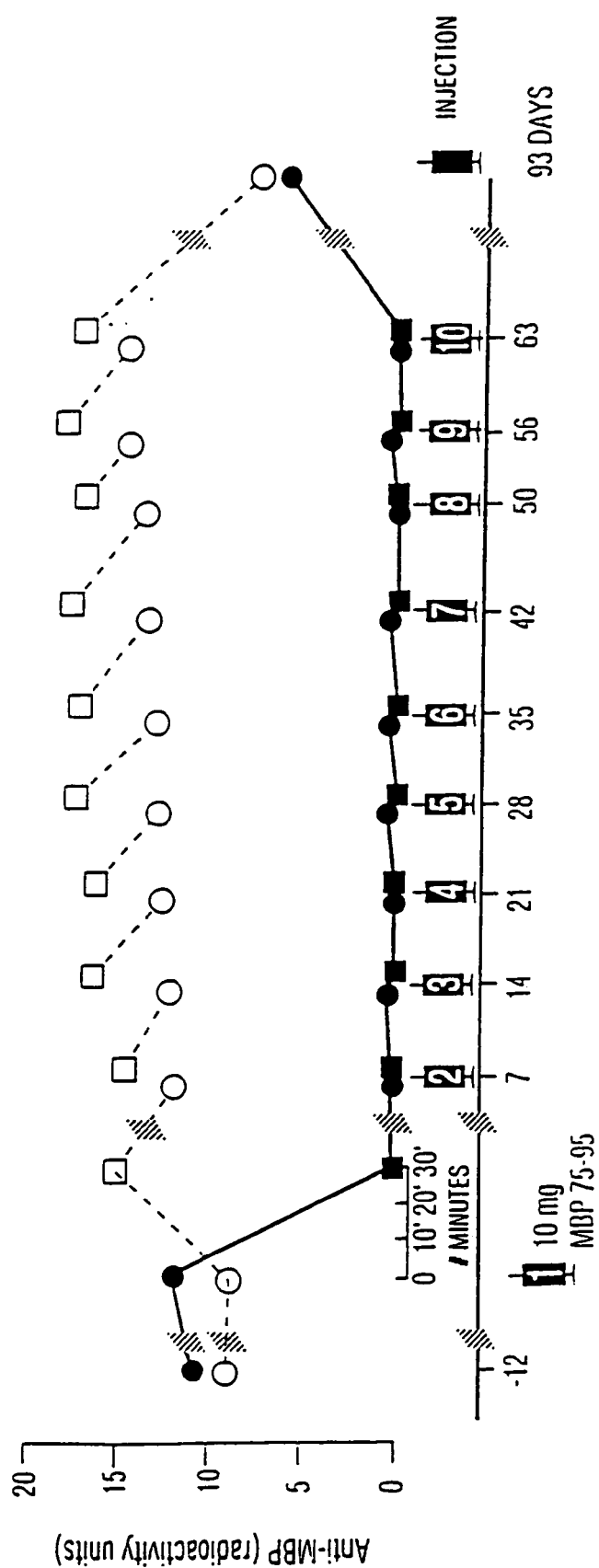

FIG. 8—Repeated intrathecal synthetic peptide injections: a patient with chronic progressive MS received 10 weekly injections of 10 mg MBP75-95 inoculated directly into the CSF; F and B titers of anti-MBP were measured before (circles) and 30 minutes after (squares) each inoculation. F anti-MBP (closed circles and squares) was rendered undetectable for the 10 week period while B antibody remained essentially unchanged (open circles and squares).

Figure 9:
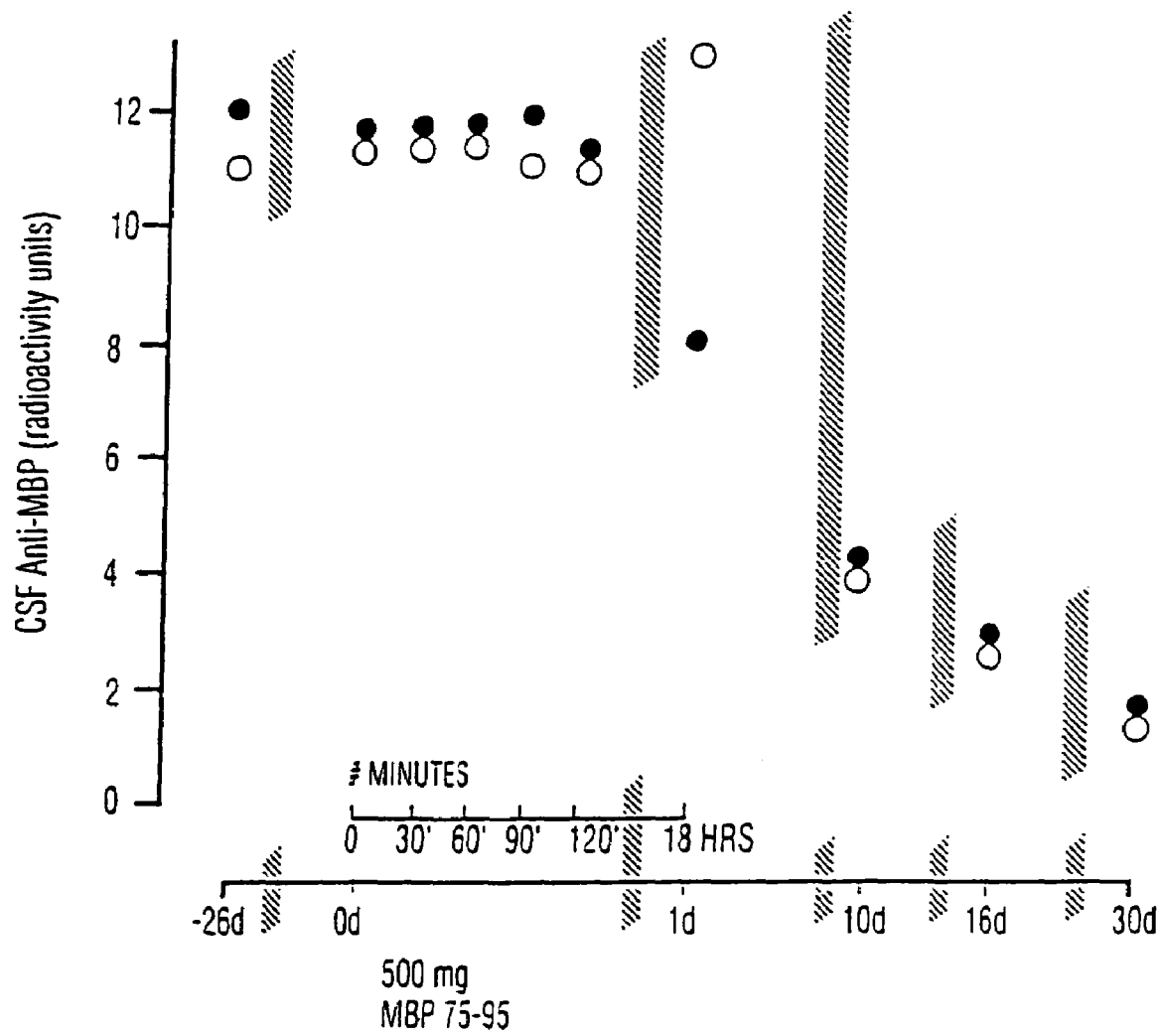

FIG. 9—Intravenous synthetic peptide administration: CSF anti-MBP levels following a single intravenous injection of 500 mg MBP75-95; both F and B anti-MBP levels declined significantly when tested 10, 16 and 30 days after injection. Symbols as in FIG. 4.

Figure 10:
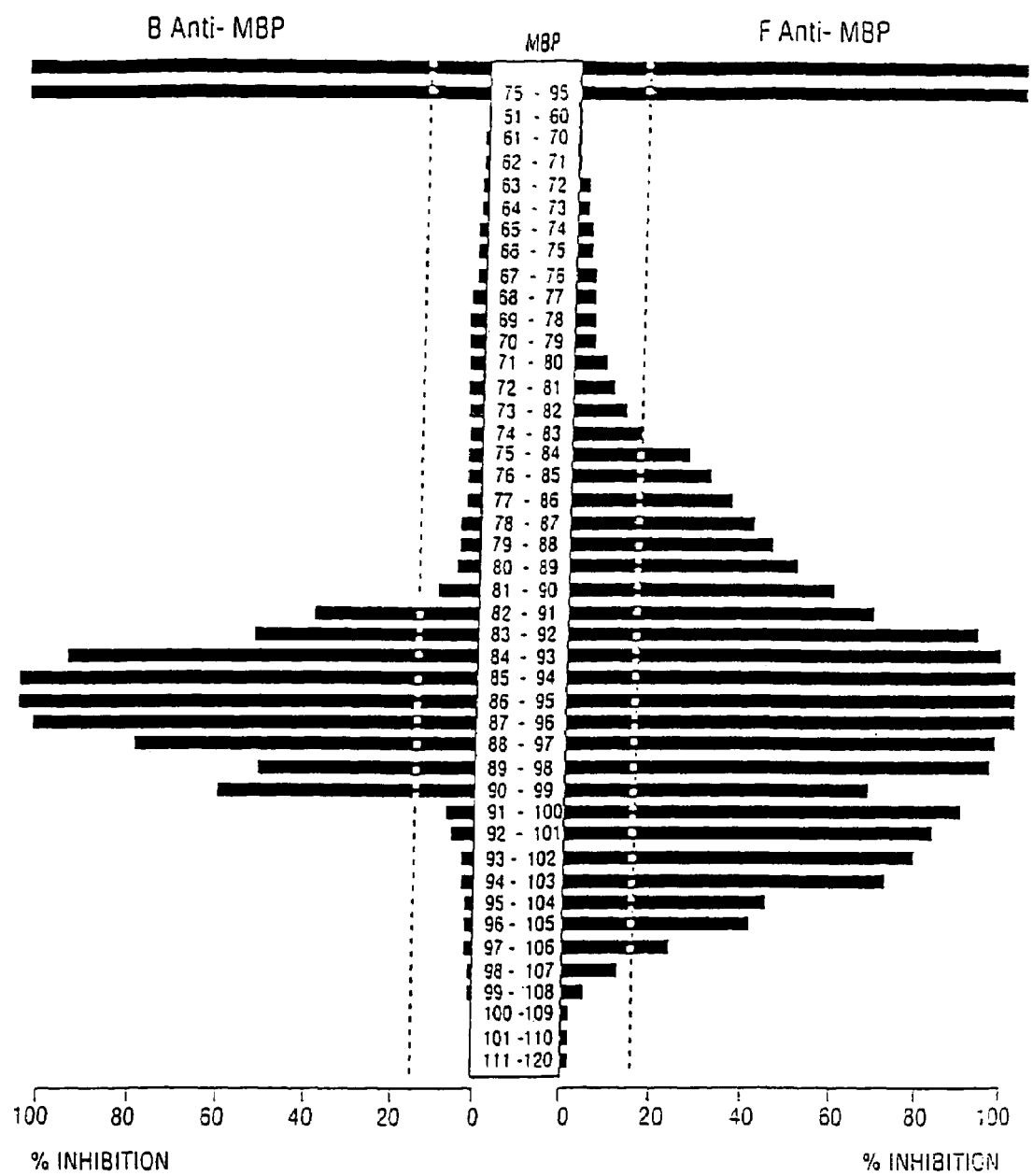
Figure 11A:
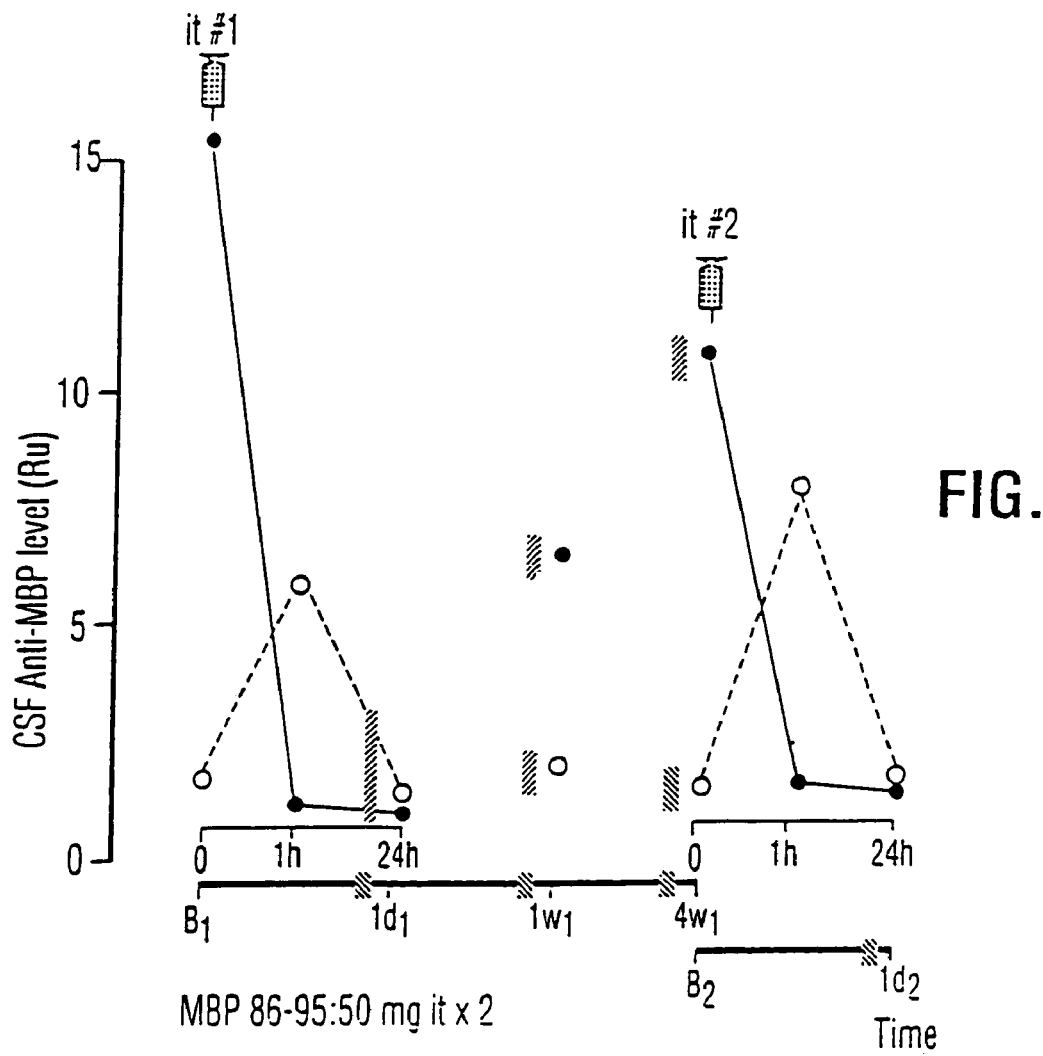

FIG. 10.—Further refinement of the MBP epitope for MS anti-MBP using a set of 41 decapeptides which covered the area between residues 61 and 110. Legend:

bars represent percent inhibition=100 –radioactivity units
MBP and peptide MBP75-95 were used as positive controls and produced complete (100%) inhibition of both F and B antibody
peptides MBP51-60 and MBP 111-120 were used as negative controls and produced insignificant inhibition (0-10%) of F and B anti-MBP
decapeptides MBP84-93, MBP85-94, MBP86-95 and MBP87-96 which produced maximum inhibition (90-100%) of both F and B antibody are highly associated with the MBP epitope
dotted line: 95% confidence limits of the inhibition assay FIG. 11a shows free (F)-● and bound (B)-○ CSF anti-MBP in a patient with unilateral optic neuritis who received intrathecally two injections (it#1 and it#2) of 50 mg pMPB86-95, 4 weeks apart; w=number of weeks.

Figure 11B:
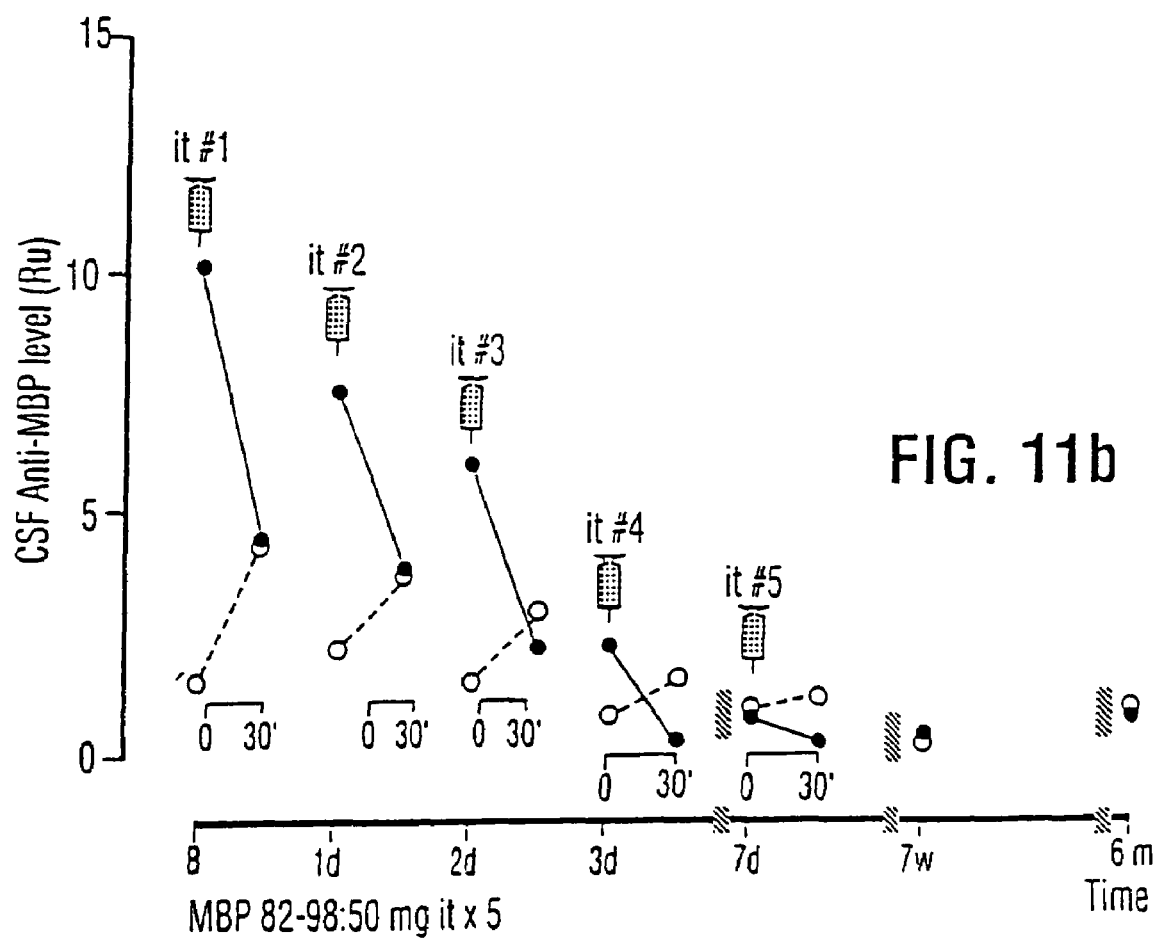

FIG. 11b shows free (F)-● and bound (B)-○ CSF anti-MBP levels in a patient with complete unilateral optic neuritis who received multiple intrathecal injections (it#1, it#2, it#3, it#4 and it#5) of 50 mg pMBP82-98 during the first week of relapse.

Figure 11C:
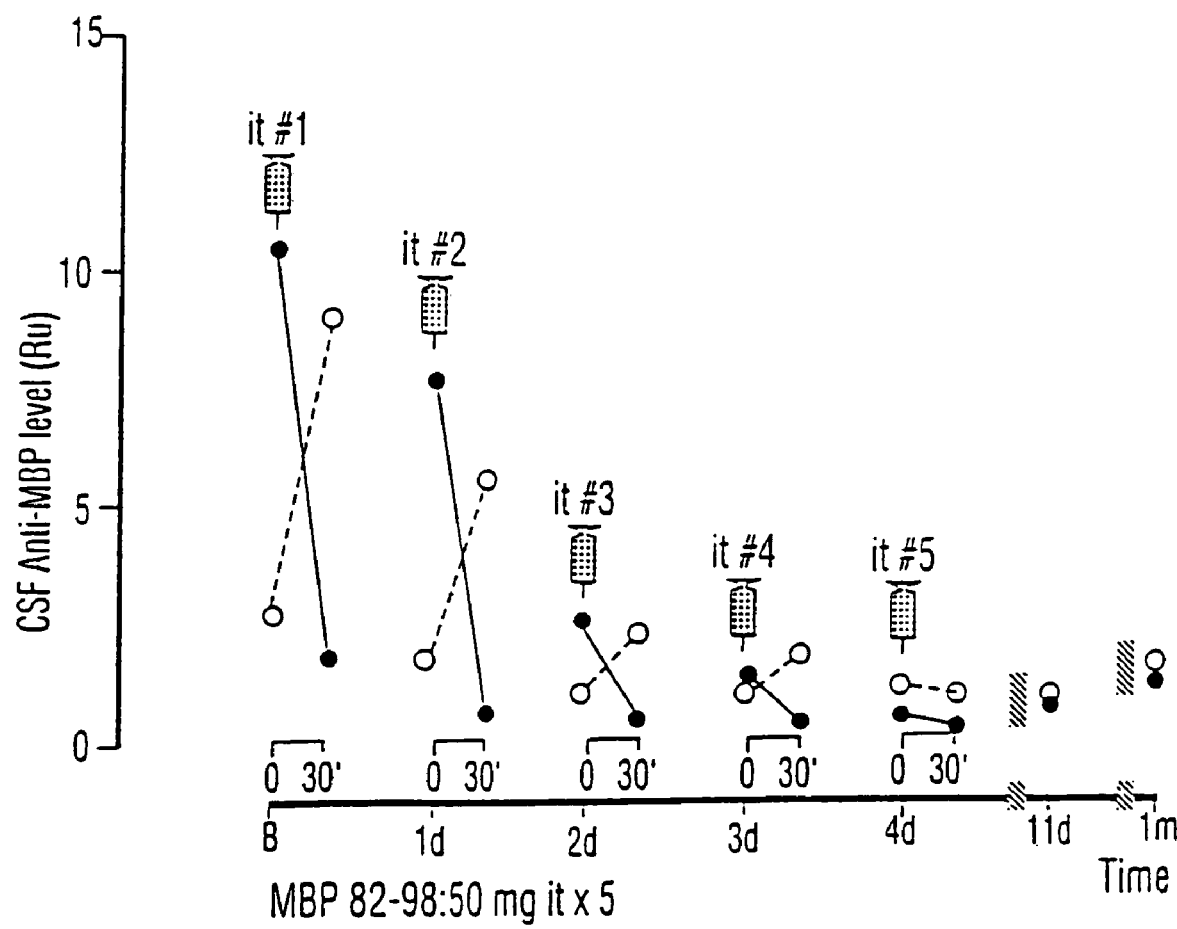

FIG. 11c shows free (F)-● and bound (B)-○ CSF anti-MBP levels in a patient with pseudoatherosis who received five daily intrathecal injections (it#1, it#2, it#3, it#4 and it#5) of 50 mg pMBP82-98.

Figure 11D:
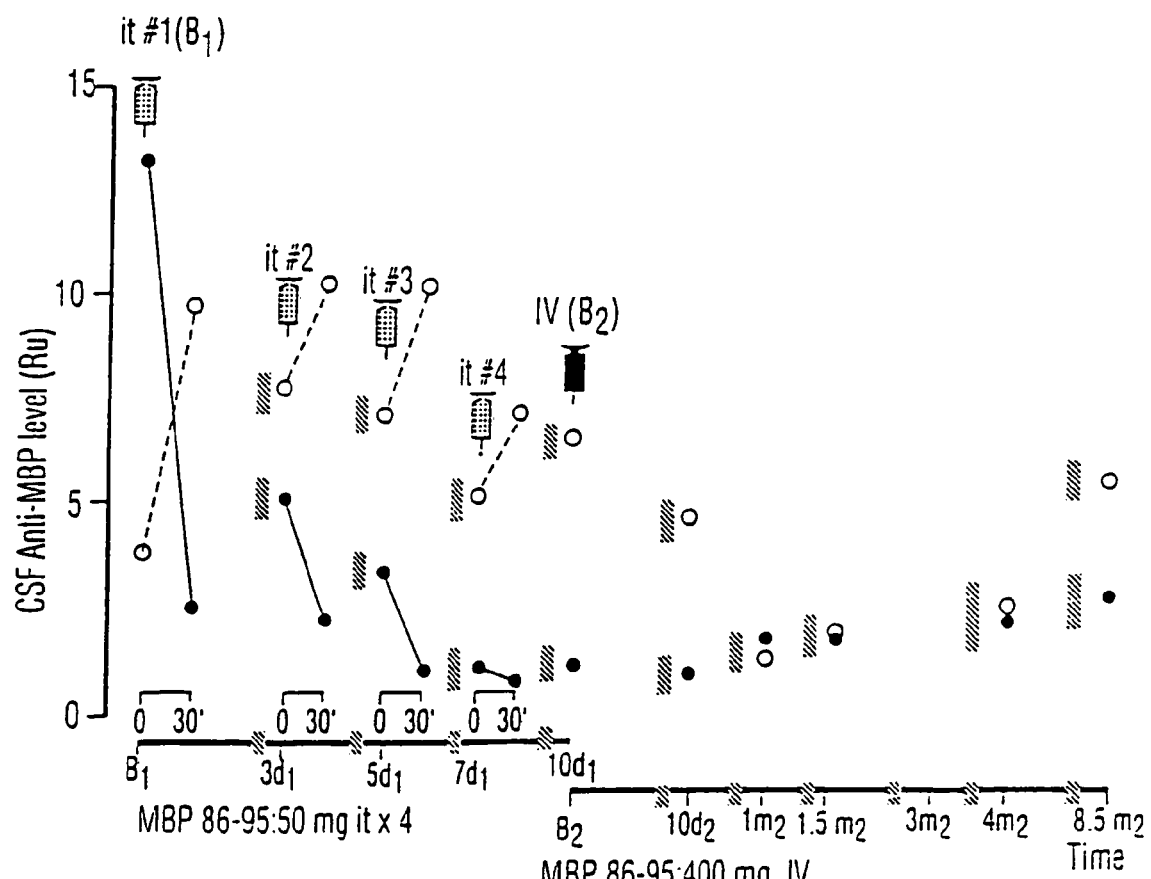

FIG. 11d shows free (F)-● and bound (B)-○ CSF anti-MBP levels in a patient with relapsing-progressive MS who received four intrathecal injections (it#1, it#2, it#3 and it#4) of 50 mg pMPB86-95 every 2 to 3 days during the first week of a relapse and one intravenous injection (IV) of 400 mg pMPB86-95 when the disease reentered the progressive phase.

Figure 12:
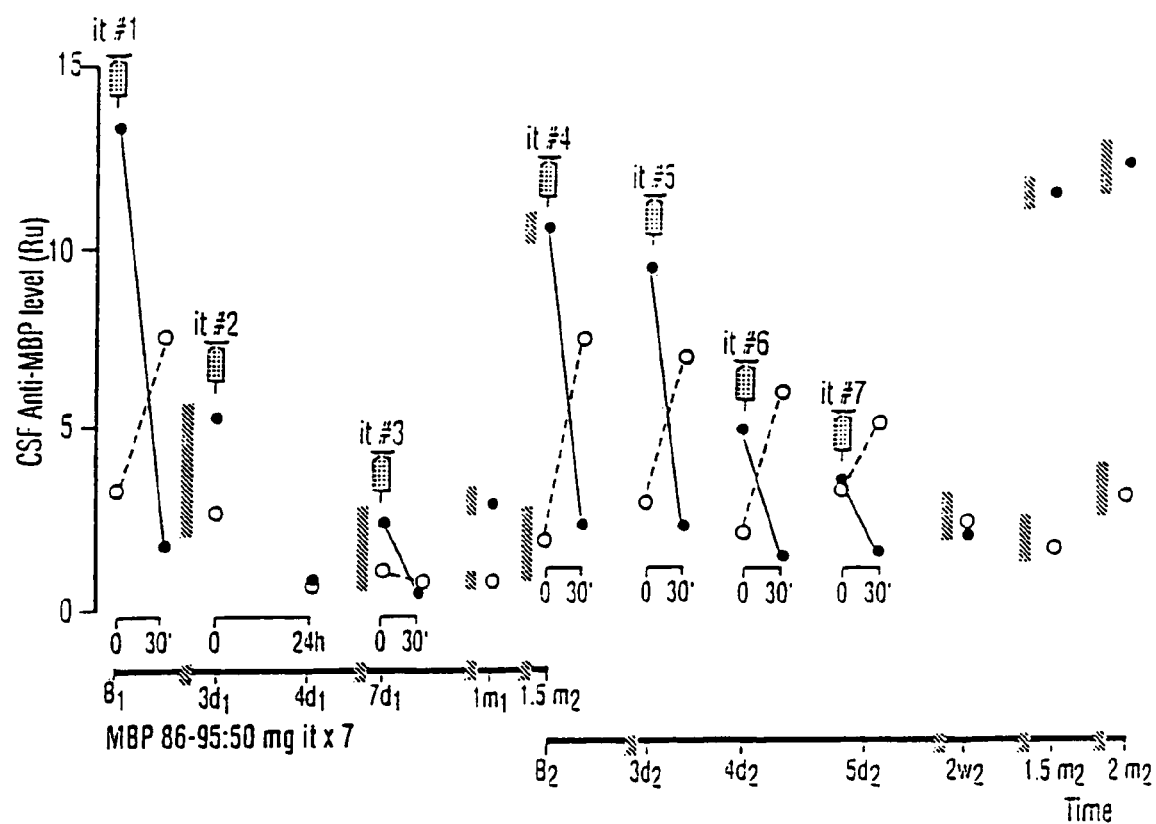

FIG. 12 shows free and bound CSF anti-MBP levels in a patient with a polysymptomatic relapse who received a total of seven intrathecal injections of 50 mg pMPB86-95. No CSF sample was obtained 30 minutes after it#2; a CSF sample was obtained 24 hours later. Symbols as in FIG. 11.

Figure 13:
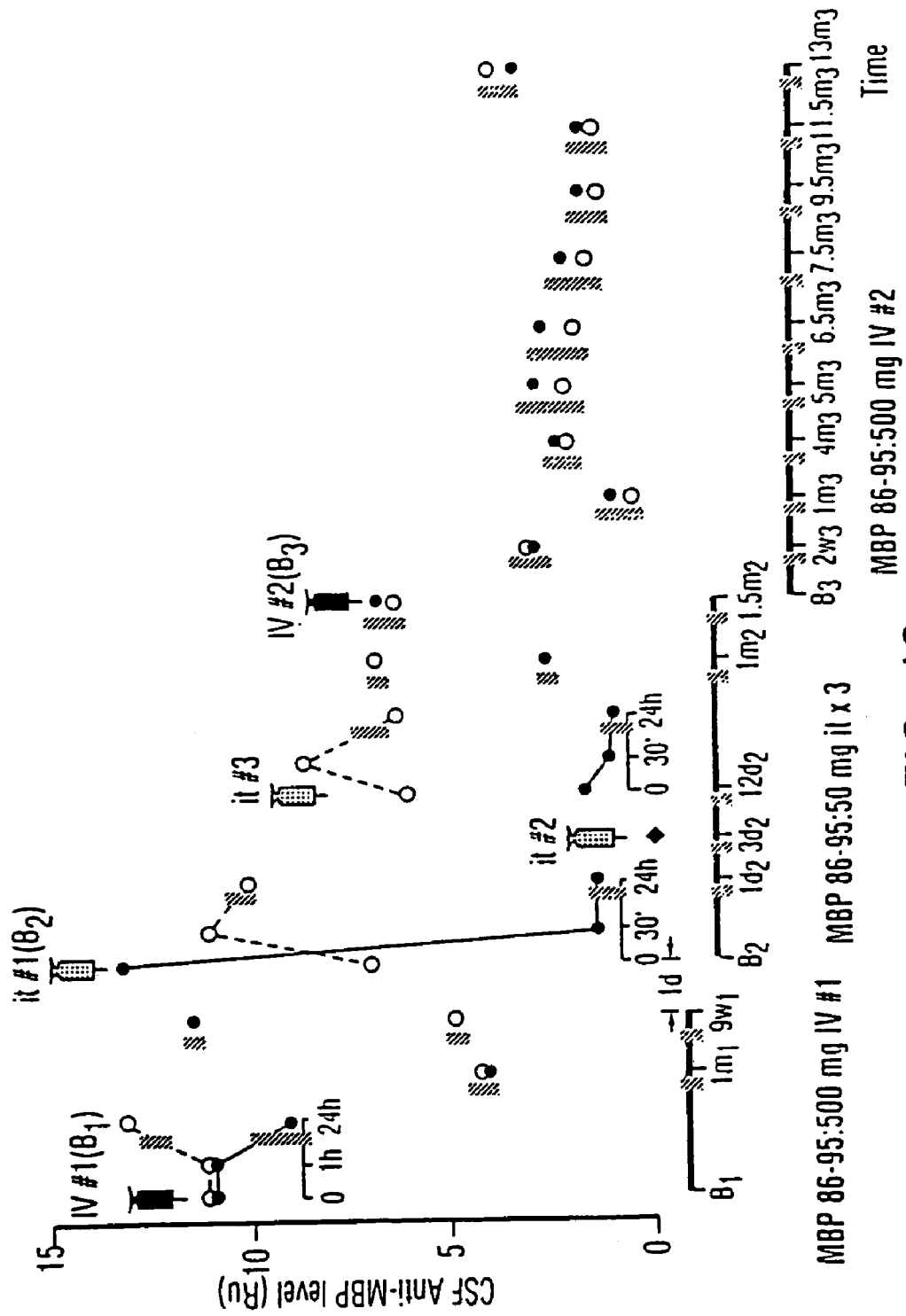

FIG. 13 shows free and bound CSF anti-MBP levels in a patient with relapsing-progressive MS who received both intrathecal (it#1, it#2 and it#3) and intravenous (IV#1 and IV#2) injections of pMPB86-95. No CSF sample was obtained before or after it#2. Symbols as in FIG. 11.

Figure 14:
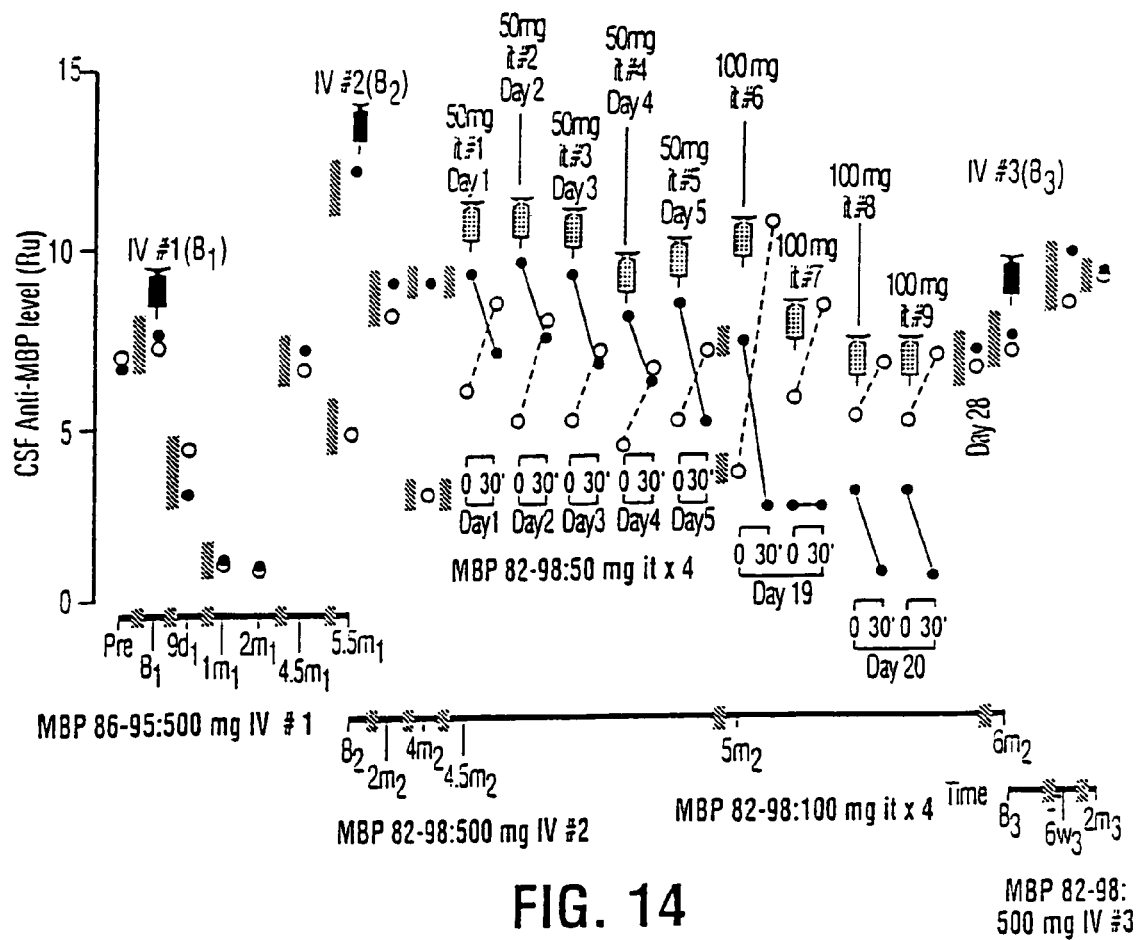

FIG. 14 shows free and bound CSF anti-MBP levels in a patient with relapsing-progressive MS who received intravenous (IV#1, IV#2 and IV#3) and intrathecal (it#1 to it#9) injection of pMPB86-95 and pMBP82-98. Symbols as in FIG. 11.

Figure 15:
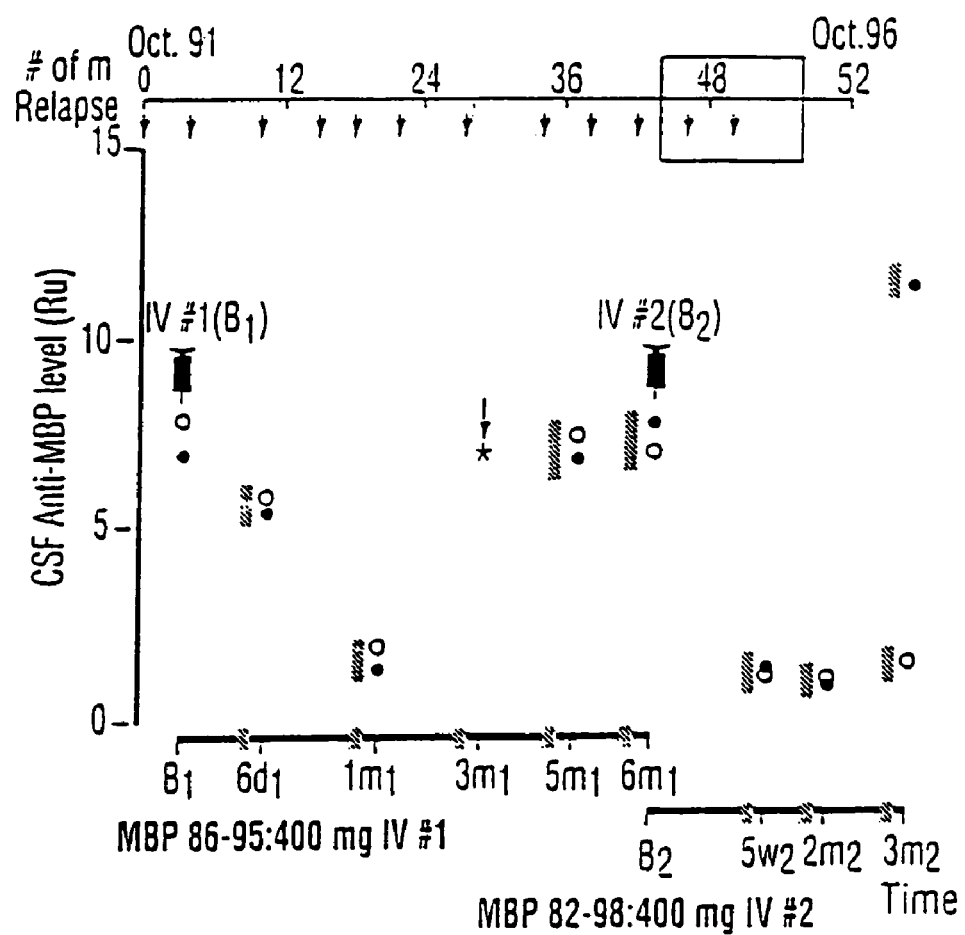

FIG. 15 shows the attempt to prevent future relapses in a patient with relapsing-progressive MS who received two intravenous injections (IV#1 and IV#2) of 400 mg pMPB86-95 and pMBP82-98. No CSF sample was obtained during the first relapse, 3 months after IV#1. Natural rate of relapses is represented at the top by arrows corresponding to the month of the attack. Boxed area represents the time of the experiment. Symbols as in FIG. 11.

Figure 16:
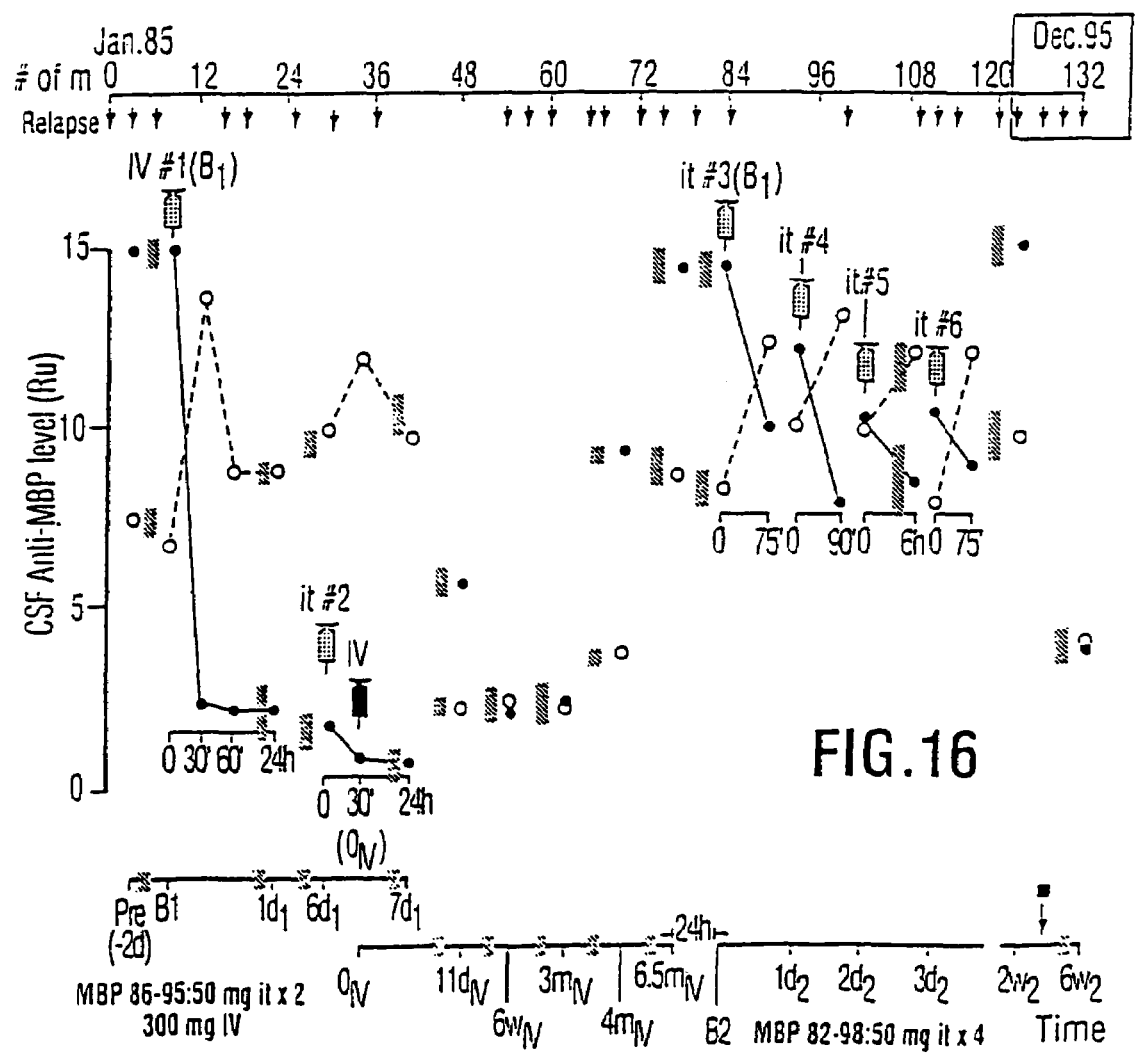

FIG. 16 hows the attempt to prevent future relapses in a patient with relapsing-progressive MS who received two intrathecal (it#1 and it#2) and one intravenous injection (IV) of pMPB86-95. ■, high dose of intravenous methylprednisolone. Natural rate of relapses is represented at the top by arrows corresponding to the month of the attack. Boxed area represents the time of the experiment. Symbols as in FIG. 11.

Figure 17A:
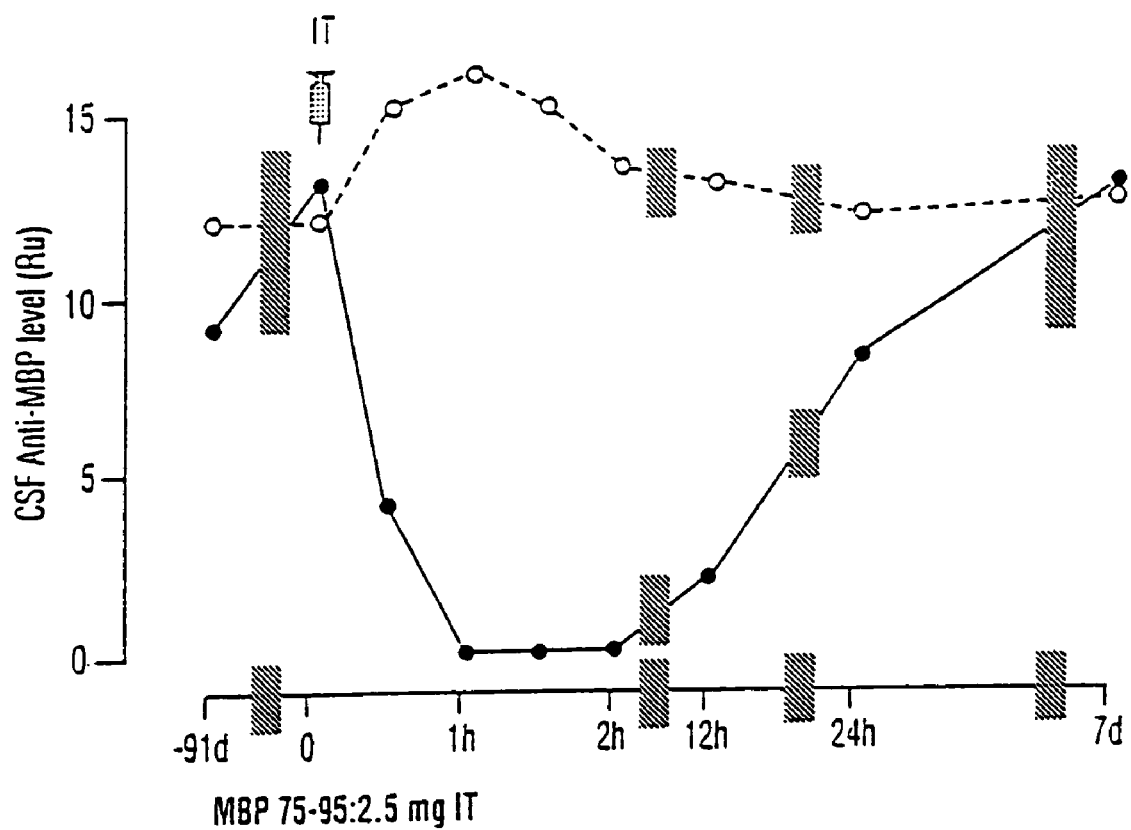
Figure 17B:
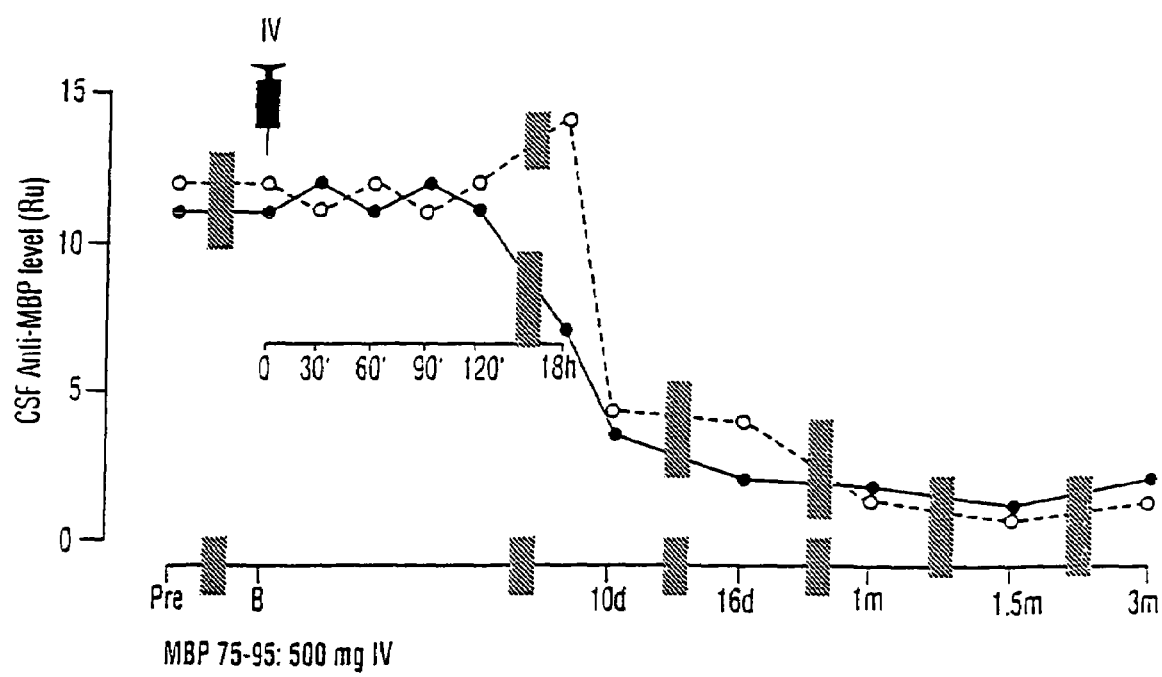

FIG. 17 shows the effect of intrathecal and intravenous peptide administration of MBP specific autoantibodies in CSF of a chronic progressive MS patient; wherein in FIG. 17a pMBP75-95 was injected directly into CSF (2.5 mg in 5 ml of saline) and MBP specific autoantibodies were measured by a solid-phase radioimmunoassay at different time points (0.5 hours to 7 days following injection). Peptide injection resulted in transient neutralization of free anti-MBP (closed circles) but did not affect bound anti-MBP (open circles). Autoantibodies were undetectable at 1 and 2 hours and started to return to baseline values between 12 and 24 hours following injection. Similar observations were made in seven other chronic progressive MS patients. In FIG. 17b, thirteen months following intrathecal peptide injection shown in FIG. 17a, 500 mg of pMBP75-95 were injected intravenously in 50 ml of saline and MBP specific autoantibodies in CSF were measured over a 3 month period (mean±standard deviation).

Figure 18:
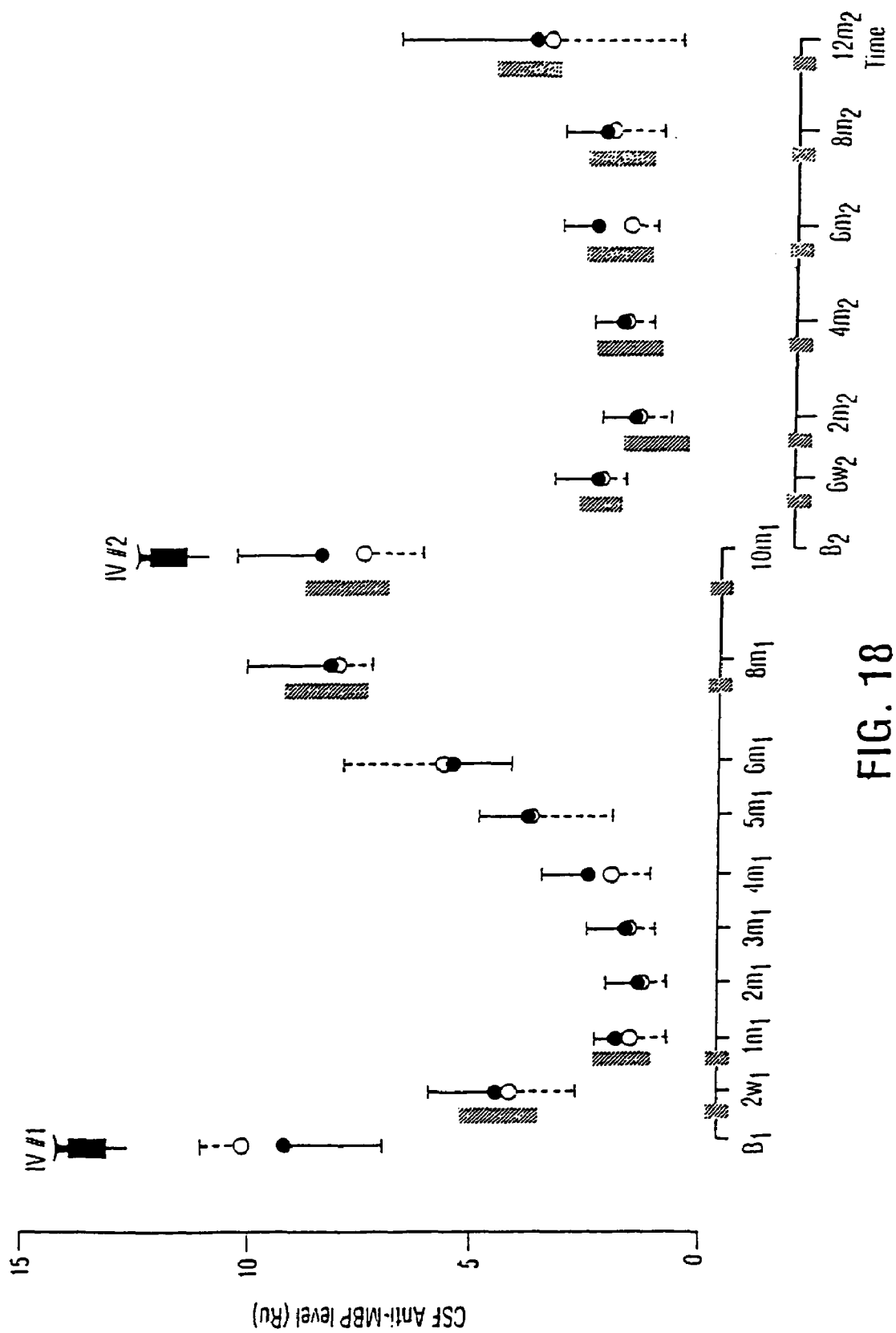

FIG. 18 shows a composite of CSF anti-MBP levels in thirteen patients with chronic progressive MS who were given an intravenous injection (IV#1 of 5 to 6 mg/kg body weight (256-500 mg in normal saline) of pMBP75-95 (2 patients) or pMBP86-95 (11 patients); both free and bound anti-MBP (closed and open circles, respectively) were determined. Autoantibody levels were low or undetectable between one and four months after IV#1, when they started to return to baseline levels. Between 6 and 10 months after IV#1, all patients received a second intravenous injection of pMBP82-98 at the same dose (IV#2).

DETAILED DESCRIPTION OF THE INVENTION

The present invention is directed to selected peptides, which are substantially homologous in sequence to a part of the amino acid sequence of a human myelin basic protein. By 'substantially homologous' it is meant that some variation between the amino acid sequence of human myelin basic protein and the peptides can exist provided that the peptides, with a variation in amino acid sequence, still function in their intended use, i.e. to down regulate the production of antibodies to human myelin basic protein (anti-MBP). Given the teachings of the present invention, it would be readily apparent to persons skilled in the art to determine, empirically, what variation can be made to the sequence of the selected peptides without affecting the function of the peptides.

Based on further work related to the present invention, on the basis of the competitive inhibition assays using a series of 41 decapeptides, the MBP epitope for MS anti-MBP has been refined and localized to an area between amino acid 86 and amino acid 95. Based on the highest level of inhibition, (equal or greater than 95%) of B-anti MBP, the MBP epitope for MS anti-MBP is between amino acid 86 and amino acid 95. The smallest common region of the effective decapeptides is from amino acid 87 to amino acid 93. Thus, according to the present invention, the peptides can be illustrated by the following formula:

$R_1$-Val-His-Phe-Phe-Lys-Asn-Ile-$R_2$ (SEQ ID NO:2)

and salts thereof, wherein $R_1$ and $R_2$ are independently selected from the group consisting of hydrogen, hydroxy, the residue of an amino acid and the residue of a polypeptide; provided that $R_1$ and $R_2$ are not both hydrogen or hydroxyl at the same time.

The 7 amino acids spanning amino acid position 87 to 93 would probably not be large enough to effectively bind anti-MBP. Thus, $R_1$ and $R_2$ cannot both be hydrogen or both be hydroxy at the same time.

When $R_1$ or $R_2$ is an amino acid, the amino acid can be selected from naturally occurring amino acids. $R_1$ or $R_2$ are not restricted to the amino acids occurring upstream or downstream of Val87 and Ile93 in the human myelin basic protein, as shown in SEQ ID NO: 1. Various modifications, including substitutions, additions or deletions in the upstream and downstream sequences of $R_1$ and $R_2$ can be used. In addition, modification, including substitutions, additions or deletions can be made to the sequence -Val-His-Phe-Phe-Lys-Asn-Ile, (SEQ ID NO:2) provided that the peptides so produced still function in their intended use; i.e., to neutralize or modulate the production of antibodies to myelin basic protein.

The term "residue of polypeptide" or "polypeptide residue" is meant to include different size polypeptides including proteins or fragments thereof. As above, when $R_1$ or $R_2$ is a polypeptide residue, $R_1$ or $R_2$ are not limited to the peptides occurring upstream or downstream of Val87 and Ile93, in the human myelin basic protein. Any polypeptide residue can be used.

In one embodiment of the invention $R_1$ can be a peptide selected from the group of peptides ranging from amino acid residue 61 to amino acid residue 86 of SEQID No:1. The length of said peptide can range from a single amino acid residue to a 26 amino acid residue.

In a further embodiment of the present invention $R_2$ can be a peptide selected from the group of peptides ranging from animo acid residue 94 to amino acid residue 106 of SEQID No:1. The length of said peptide can range from a single amino acid residue to a 13 amino acid residue.

$R_1$ and/or $R_2$ could be a repeat of the sequence -Val-His-Phe-Phe-Lys-Asn-Ile, or modifications thereof, including substitutions, additions or deletions. Thus, the peptide could contain multiple copies of the anti-MBP binding site (epitope).

The compounds of the present invention can be prepared according to widely acceptable methods of synthesizing polypeptides. Also included within the scope of the term 'peptide' are peptides produced by recombinant DNA technology. Knowing the sequence of the selected peptides, as disclosed in the present invention, it is within the scope of the present invention to determine an appropriate DNA sequence, which will code for the selected amino acid sequence. The appropriate DNA sequence can be produced by conventional, known methods of synthesizing DNA sequences. The DNA sequences so produced can then be cloned into appropriate cloning vehicles and used to transform an appropriate host cell to produce the recombinant peptide. All of the methodology referred to above is conventional and well-known to persons skilled in the art.

The peptides, of the present invention, are substantially homologous in sequence to a part of the amino acid sequence of human myelin basic protein. B 'a part of the amino acid sequence' it is meant that the sequence can be of any length provided that the amino acid sequence is long enough to function to down regulate production of anti-human myelin basic protein but not of a length which would result in prior art problems when MBP peptides were used for in vivo treatment of Multiple Sclerosis. According to the present invention the peptides can be at least 10 amino acids in length. In one example of the present invention the peptides can be from about 10 amino acid residues to about 25 amino acid residues. If the peptides of the present invention are used as part of a fusion protein, the overall size of the peptide can be much larger.

According to one embodiment of the present invention it has been determined that selected peptides substantially corresponding to the amino acid sequence of h-MBP are effective in down regulating production of anti-MBP. These peptides correspond to the amino acid sequence of h-MBP from about residue 61 to about 106. In one example these peptides correspond to the amino acid sequence of the h-MBP from residue 75 to about residue 106, when the peptides are used for the neutralization of free anti-MBP. In a further example, these peptides correspond to the amino acid sequence of the h-MBP from about residue 82 to about residue 99, when the peptides are used for neutralization of F anti-MBP or down regulation of synthesis of F and B anti-MBP. Therefore the peptides are selected from 10 amino acid residues to 25 amino acid residues taken from a continuous amino acid sequence within the sequence shown below (SEQID NO:1), provided that said sequence can neutralize or modulate the production of the anti-myelin basic protein.

SEQ ID NO: 14
61
His His Pro Ala Arg Thr Ala His Tyr Gly Ser Leu

Pro Gln Lys Ser His Gly Arg Thr Gln Asp Glu Asn

Pro Val Val His Phe Phe Lys Asn Ile Val Thr Pro

Arg Thr Pro Pro Pro Ser Gln Gly Lys Gly

106

Examples of peptides are selected from the group consisting of:
(SEQ ID NOS:5, 4, 6, 3, 7 and 8, Respectively)

MBP61-75
His His Pro Ala Arg Thr Ala His Tyr Gly Ser Leu
Pro Gln Lys

MBP64-78
Ala Arg Thr Ala His Tyr Gly Ser Leu Pro Gln Lys
Ser His Gly

MBP69-83
Tyr Gly Ser Leu Pro Gln Lys Ser His Gly Arg Thr
Gln Asp Glu

MBP75-95
Lys Ser His Gly Arg Thr Gln Asp Glu Asn Pro Val
Val His Phe Phe Lys Asn Ile Val Thr

MBP80-97
Thr Gln Asp Glu Asn Pro Val Val His Phe Phe Lys
Asn Ile Val Thr Pro Arg

MBP91-106
Lys Asn Ile Val Thr Pro Arg Thr Pro Pro Pro Ser
Gln Gly Lys Gly

In one embodiment of the present invention, the peptides are represented by the formula:

$$R_1\text{-Val-His-Phe-Phe-Lys-Asn-Ile-}R_2$$

(SEQ ID NO:2)

and salts thereof, wherein $R_1$ and $R_2$ are independently selected from the group consisting of hydrogen, hydroxy, the residue of an amino acid and the residue of a polypeptide; provided that $R_1$ and $R_2$ are not both hydrogen or hydroxyl at the same time. The peptide can contain substitutions, deletions or additions thereof, provided that the peptide maintains its function of neutralizing or modulating the production of anti-MBP.

Examples of peptides are selected from:
(SEQ ID NOS:9 to 13)

MBP84-93
Asn Pro Val Val His Phe Phe Lys Asn Ile

MBP85-94
Pro Val Val His Phe Phe Lys Asn Ile Val

MBP86-95
Val Val His Phe Phe Lys Asn Ile Val Thr

MBP87-96
Val His Phe Phe Lys Asn Ile Val Thr Pro

MBP82-98
Asp Glu Asn Pro Val Val His Phe Phe Lys
Asn Ile Val Thr Pro Arg Thr

The peptide MBP82-98 has an improved solubility over the other peptides used in the present invention, due to the five additional hydrophilic residues in this peptide. Thus, the use of this peptide is preferred over the other peptides disclosed in the present invention.

The potential role of anti-MBP in the pathogenesis of MS continues to be explored. Increased anti-MBP titers in patients with active MS were initially reported by Panitch et al (Panitch, H. S., Hooper, C. S., and Johnson, K. P., Arch Neurol 37:206-209, 1980) who used a solid phase radioimmunoassay with guinea-pig MBP. Patients with acute MS relapses have usually increased anti-MBP predominantly in free form, while some patients in clinical remission may have undetectable anti-MBP levels. During the transition phase from an acute relapse to remission, titers of free anti-MBP progressively decrease over weeks or months, while bound fractions of the antibody rise as compared to their initial value. In other patients in remission, it is possible to observe low titers of free and bound anti-MBP, usually with a F/B ratio below unity, suggesting that anti-MBP neutralizing antibody(ies) are bound to anti-MBP. Occasionally, patients who fit the criteria of clinically definite MS or patients who had neuropathologically confirmed MS had undetectable anti-MBP during active phases of their disease. It is possible that such patients have antibodies to other myelin proteins. The absence of a specific antibody scenario does not negate the potential importance of anti-MBP in the mechanism of demyelination in the majority of MS patients.

Recently, an MBP antibody cascade was observed in the IgG fraction purified from MS CSF (Warren, K. G. and Catz, I., J Neurol Sci 96:19-27, 1990). Primary antibodies to MBP in both free and bound forms occur in association with active disease: F/B ratios are above unity in patients with acute relapses, and below unity in patients with chronic progressive disease (Warren, K. G. and Catz, I., Ann Neurol 209:20-25, 1986; Catz, I. and Warren, K. G., Can J Neurol Sci 13:21-24, 1986; and Warren, K. G. and Catz, I., Ann Neurol 21:183-187, 1987). Secondary antibodies which neutralize anti-MBP appear when the disease becomes inactive. Tertiary antibodies which inhibit anti-MBP neutralization are present when the disease is chronically progressive and fails to become inactive. The fact that an MBP antibody cascade is associated with distinct phases of MS suggests its possible importance vis-a-vie the natural history of this illness.

Although anti-MBP can be detected in CSF of patients with active MS, their direct role in the pathogenesis of demyelination remains to be confirmed. The involvement of anti-MBP in the mechanism of MS could best be determined by their down regulation, in vivo, perhaps by administration of selected peptides and monitoring the clinical course of the disease. If anti-MBP is (are) the only primary antibody(ies) associated with demyelination in MS, it may be possible to block this process by intrathecal, and/or intravenous administration, of selected MBP peptides which would down regulate anti-MBP and would promote tolerance to MBP in situ. Other human myelin proteins may also be involved with the demyelination in MS and accordingly, it is within the scope of the present invention to use peptides substantially homologous in sequence to a part of the amino acid sequence of these other myelin proteins to down regulate the corresponding antibodies. Although previous attempts to treat MS by intramuscular or subcutaneous administration of heterologous MBP have not been entirely successful (Campbell, B., Vogel, R. J., Fisher, E. and Lorenz, R., Arch Neurol 29:10-15, 1973; Gonsette, R. E., Delmotte, P. and Demonty, L. J Neurol 216:27-31, 1977; and Romine, J. S. and Salk, J., In: Hallpike, J. F., Adams, C. W. M. and Tourtelotte, W. W., eds. Multiple sclerosis. Baltimore. Williams & Wilkins, 1982:621-630), intrathecal and/or intravenous administration of MBP peptides which neutralize or down regulate the production of anti-MBP, according to the present invention, has demonstrated more beneficial results.

The animal model of MS, experimental allergic encephalomyelitis (EAE), is a T cell mediated demyelinating disease. EAE can be ameliorated by intraperitoneal inoculation of affected mice with MBP synthetic peptides (Gaur, A. et al., Science 258, 1491-1494, 1992). Furthermore, administration of high doses MBP peptides deleted autoreactive T cells and abrogated clinical and pathological signs of EAE in mice (Critchfield, J. M. et al., Science 263, 1139-1143, 1994). Even oral administration of MBP modulated EAE by inducing peripheral tolerance (Chen, W. et al., Science. 265, 1237-1240, 1194). A combination of myelin antigens or synthetic peptides of these antigens administered by intravenous and/or intrathecal routes may be required to modulate the T cells, B cells and macrophages involved in the destruction of myelin in MS patients.

Accordingly, this invention also relates to pharmaceutical compositions containing as an active ingredient a peptide as described above, either alone or in combination, in admixture with a pharmaceutical acceptable carrier. Examples of pharmaceutical acceptable carriers are well known in the art, and include for example normal saline.

The peptides of the present invention can be administered to humans for the treatment or modulation of Multiple Sclerosis. The therapeutic dose, for intravenous administration, for the treatment of MS may be from about 1.0 mg per kilogram of body weight to about 10.0 mg per kilogram of body weight; for intrathecal administration, the total dose may be from about 1 to about 100 mg. In one example of the present invention, the peptide is administered either intravenously or intrathecally, or in combination. The peptides can be administered as a single or sequential dose, as may be required.

According to the present invention intravenous administration was found to down regulate both free and bound anti-MBP; whereas, intrathecal administration was only effective in neutralizing or modulating free anti=MBP.

In one embodiment of the present invention it was found that sequential intrathecal administration of MBP peptides, could reduce F anti-MBP, and maintain its low levels for months after the peptides were injected in patients suffering from monosymptomatic relapses. In one example of this embodiment, 50 mg of a peptide of MBP was administered to a patient daily for 4 to 5 days. In yet a further example a further dose can be administered one week to two weeks following the initial injections.

While this invention is described in detail with particular reference to preferred embodiments thereof, the following examples, are offered to illustrate but not limit the invention.

EXAMPLE 1

In vitro Neutralization of Anti-Human Myelin Basic Protein

Figure 1:
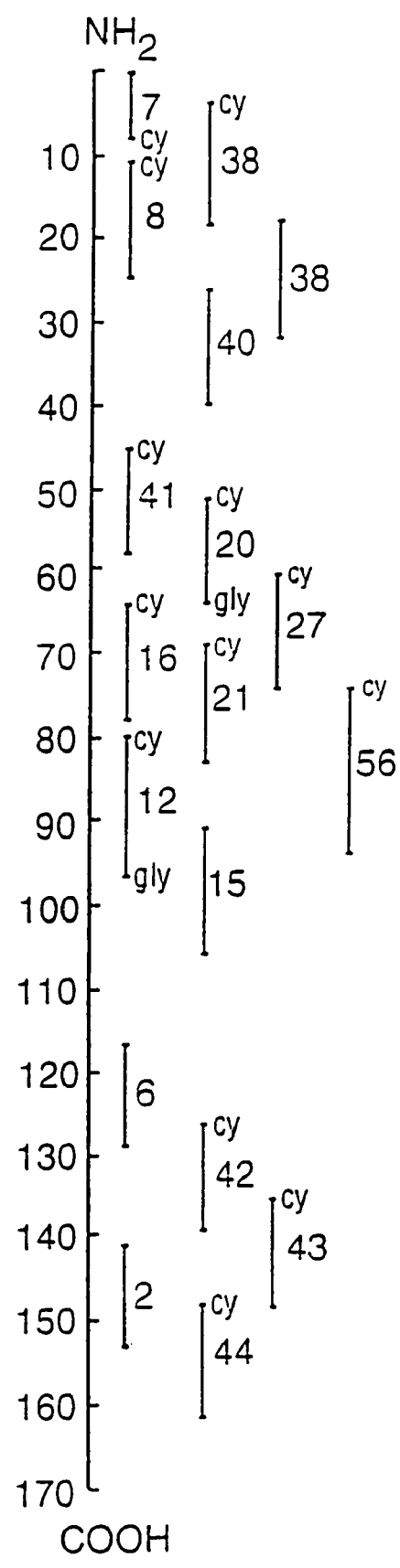
FIG. 1 shows the localization of eighteen synthetic peptides (small numbers) in relation to the intact human-MBP molecule. Peptides are represented by vertical bars placed next to their corresponding region on the MBP molecule. Large numbers represent amino acid residues on human MBP.

FIG. 1 shows the localization of 18 peptides of h-MBP used in this study in relation to the intact MBP molecule. Native MBP was isolated from non-MS brain tissue (Diebler, G. E., Martenson, R. E., Kies, M. W., Prep Biochem 2:139-165, 1972) and further purified by gel filtration and reverse phase high pressure liquid chromatography (HPLC). The final antigen preparations were checked for purity by SDS-polyacrylamide gel electrophoresis. Only preparations that migrated at the molecular weight of 18.5 KD were used in further studies. Purified MBP was used in antigen-specific affinity chromatography, in neutralization studies and in the solid phase anti-MBP radioimmunoassay.

Eighteen peptides covering the length of h-MBP and containing between 8 and 25 amino acid residues were synthesized by the Fmoc method as previously described (Groome, N. P., Dawkes, A., Barry, R. et al. J Neuroimmun 19:305-315, 1988). Peptide purity was checked by reverse-phase HPLC with a C18 column and water/acetonitrile gradient (0.1% TFA). Amino acid analysis of peptides was also performed using standard analysis. Many of the peptides used in this study contained an unnatural cysteine residue as they were made to function as immunogens in conjunction with Freund's adjuvant. This is unlikely to affect the present findings.

Cerebrospinal fluid (CSF) was obtained within a week from the onset of symptoms from 35 patients with acute MS relapses and IgG levels were determined by nephelometry. CSF samples used in this study were selected to have initially high absolute IgG levels ($\geq 0.080$ g/1) and increased titers of anti-MBP (F/B ratio>>1.0). All MS patients had clinically definite disease.

IgG was purified from concentrated CSF of patients with acute MS by protein A-Sepharose (Pharmacia™) affinity chromatography as previously described (Warren, K. G. and Catz, I., J Neurol Sci 96:19-27, 1990). The purity of each IgG preparation was checked by polyacrylamide gel electrophoresis and isoelectric focusing. When elevated anti-MBP levels from purified IgG were absorbed to zero with MBP, the post-absorption supernatants contained residual IgG indicating that anti-MBP represents only a fraction of the elevated IgG.

Purified MBP was coupled to CNBr-activated Sepharose 4B (Pharmacia™) according to the manufacturer's instructions. Purified CSF IgG containing increased anti-MBP levels from 35 patients with acute MS relapses was used to isolate anti-MBP by MBP-Sepharose affinity chromatography (Warren, K. G. and Catz, I., J Neurol Sci 103:90-96, 1991). Purified anti-MBP samples were compared with the initial IgG source by poly-acrylamide gel electrophoresis. When purified anti-MBP samples were absorbed to zero with MBP, the post-absorption supernatants contained no residual IgG indicating the purity of anti-MBP.

Constant amounts of anti-MBP (15 radioactivity binding units corresponding to 100 for scale expansion purposes=% 0) were incubated with increasing amounts of h-MBP (0-1000 ng) or individual peptides of MBP (0-10,000 ng) in a liquid phase assay and after 1.5 hours incubation, free anti-MBP levels were determined in all mixtures. Anti-MBP isolated from 7 individual MS patients or pooled anti-MBP from 10 different MS patients were used in neutralization experiments. Calf thymus histone and human serum albumin were used as negative antigen controls (range: 10-1000 ng).

One monoclonal antibody (MAb) to peptide MBP64-78 and a polyclonal rabbit antiserum to peptide MBP1-8 were used as positive antibody controls (Groome, N., Harland, J., and Dawkes, A., Neurochem Int 7:309-317, 1985; Barry, R., Payton, M., and Groome, N., Neurochem Int 2:291-300, 1991). Another mouse monoclonal antibody to epitope 45-50 was used as negative antibody control.

Anti-MBP levels were determined by a solid phase radioimmunoassay with human MBP (Warren, K. G. and Catz, I., Ann Neurol 209:20-25, 1986; Warren, K. G. and Catz, I., Ann Neurol 21:183-187, 1987; and Warren, K. G. and Catz, I., J Neurol Sci 91:143-151, 1989). Free anti-MBP levels were measured in all fractions from affinity chromatography and in all neutralization mixtures. All individual samples were run in quadruplicate using the same iodinated material in order to minimize between-assay variability.

Figure 2:
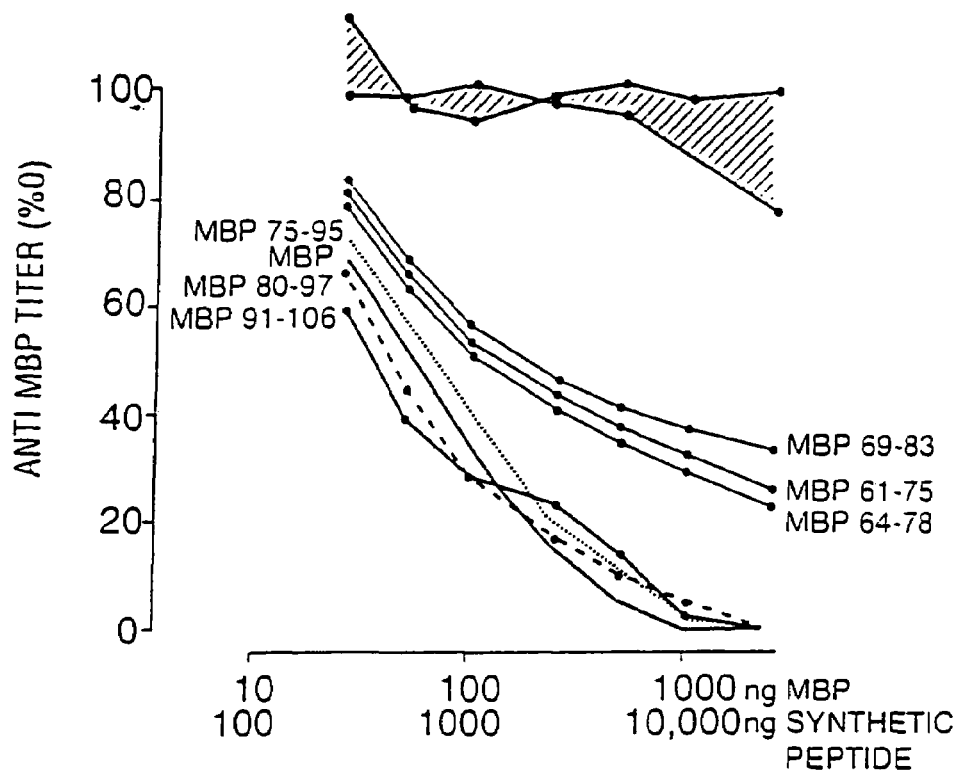
FIG. 2 shows inhibition curves of anti-MBP, purified and pooled from 10 different multiple sclerosis patients, by human MBP and MBP-peptides.

Purified anti-MBP was completely neutralized by MBP and by peptides MBP80-97, MBP91-106 and MBP75-95, and was partially neutralized by peptides MBP64-78, MBP69-83 and MBP61-75 (Table 1 and FIG. 2). The remaining twelve peptides did not neutralize purified anti-MBP and their kinetic curves fell within the striped area shown in FIG. 2. Calf thymus histone and human serum albumin did not react with purified anti-MBP even at concentrations as high as 1000 ng. The MAb to peptide MBP64-78 was only inhibited by peptide MBP64-78, and the MAb to peptide MBP 1-8 was only inhibited by peptide MBP1-8. The MAb peptide MBP 45-50 did not react with MBP or any of the peptides (for clarity of the figure, control data are not illustrated). The control samples demonstrate the validity of the neutralization approach as each control antibody was neutralized completely by the expected peptide and by none of the other peptides. This shows that even the high peptide concentrations (10,000 ng) specificity of recognition was observed.

TABLE 1

| HUMAN MBP SEQUENCE | REACTIVITY WITH ANTI-MBP |
|---|---|
| 1-170 | ++ |
| 1-8 Cy | − |
| Cy 4-18 | − |
| Cy 11-24 | − |
| 18-32 | − |
| 26-40 | − |
| Cy 35-58 | − |
| Cy 51-64 Gly | + |
| Cy 64-78 | + |
| Cy 61-75 | + |
| Cy 69-83 | ++ |
| Cy 75-95 | ++ |
| Cy 80-97 Gly | ++ |
| Cy 91-106 | − |
| 117-129 | − |
| Cy 127-140 | − |
| Cy 136-149 | − |
| 141-155 | − |
| Cy 149-162 | |

++ complete neutralization
+ partial neutralization
− insignificant reactivity

Figure 3:
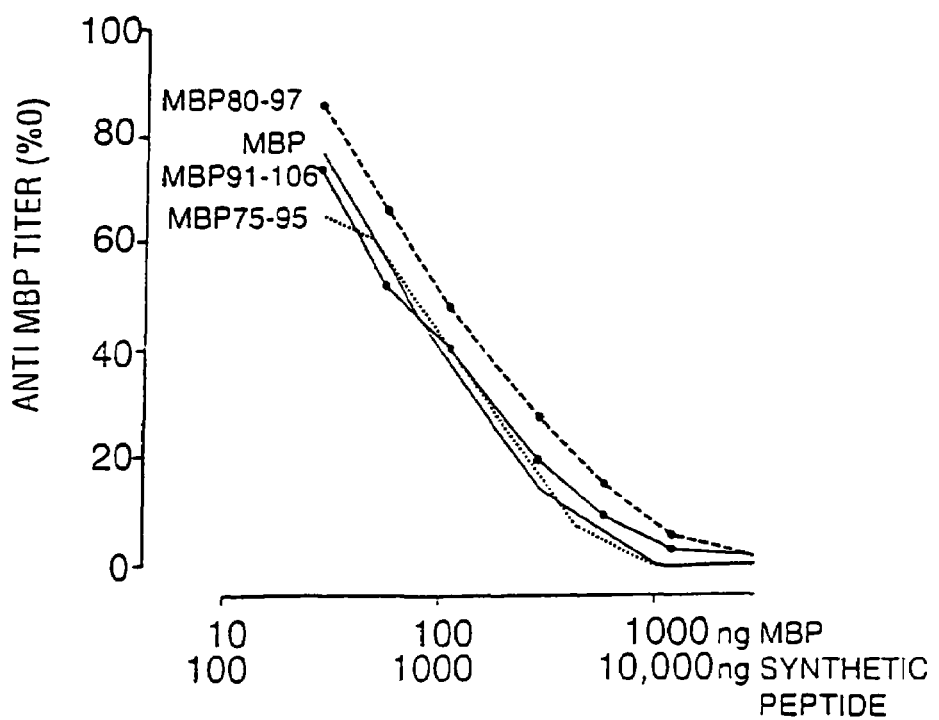
FIG. 3 shows the neutralization of anti-MBP isolated from an individual multiple sclerosis patient by human MBP and peptides MBP80-97; MBP91-106 and MBP75-95.

Anti-MBP purified from 7 individual MS patients was completely neutralized by h-MBP and peptides MBP80-97, MBP91-106 and MBP75-95 (see FIG. 3 as an illustrative example). Due to the limited amount of antibody obtained from individual MS patients, anti-MBP was not reacted with the remaining 15 peptides.

As noted previously, anti-MBP was neutralized with peptides spanning from about amino acid residue 61 to about amino acid residue 106. The peptides which did not neutralize anti-MBP cover both the amino (about residues 1 to 63) and the carboxyl (about residues 117 to 162) terminals of h-MBP. It appears that peptides from different non-overlapping regions of MBP neutralize the same antibody (ies). This might be explained if the antibodies recognize a discontinuous (assembled) epitope containing amino acids from different regions. A similar phenomenon has been previously observed by Hruby et al (Hruby, S., Alvord, E. C., Groome, N.P. et al, Molec Immun 24: 1359-1364, 1987) who showed that a rat monoclonal antibody had a major epitope in MBP sequence 112-121 but a strong cross-reaction with another epitope in peptide 39-91. This is more likely than the possibility that the antibody is cross-reactive with two completely different sequences which did not form a discontinuous epitope (Hruby, S., Alvord, E. C., Martenson, R. E., et al. J Neurochem 44:637-650, 1985). The neutralization data could be explained by the ability of peptides from different sections of MBP to each partially occupy the antibody binding pocket by interacting with different antibody amino acid side chains. This explanation fits the observation that the peptides giving complete inhibition (MBP80-97, MBP91-106 and MBP75-95) are approximately 100 times less effective on a molar basis than intact MBP at causing inhibition. By the hypothesis advanced above, this could be due to each peptide clone being unable to achieve the binding energy of the original MBP epitope.

EXAMPLE 2

Figure 4:
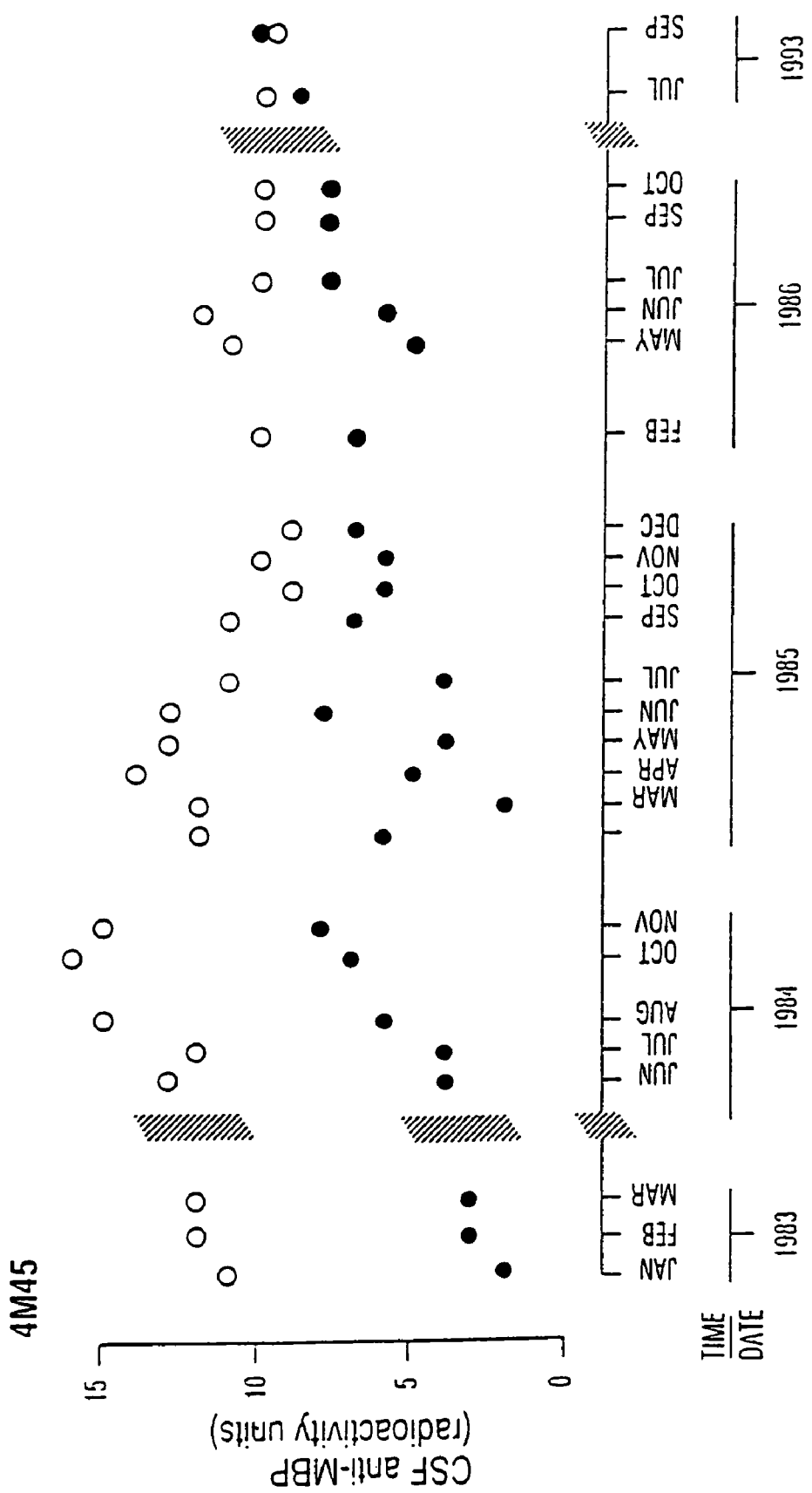
FIG. 4—Longitudinal monitoring of CSF anti-MBP titers in a patient with chronic progressive MS:
  F (Free) and B (Bound) levels of anti-MBP were persistently elevated when sampled 26 times over a period of 11 years from 1983 to 1993.

In vivo Neutralization or Modulation of Production of Anti-Human Myelin Basic Protein Patient Selection and Control Studies Patients who participated in this research project were seen in the Multiple Sclerosis Patient Care and Research Clinic of the University of Alberta, Edmonton, Canada. The patients have been diagnosed as having clinically definite multiple sclerosis by Schumacher criteria (1965) confirmed by magnetic resonance imaging of the brain and CSF immunochemistry profiles. In order to illustrate that in chronic progressive MS anti-MBP was persistently elevated over long periods of time, months to years, patients had repeated lumbar punctures with monitoring of F and B anti-MBP. In a patient with chronic progressive MS, it was observed that the autoantibody remained persistently elevated for periods as long as 11 years and that spontaneous decline of anti-MBP levels did not occur (FIG. 4 is an illustrative example).

Figure 5A:
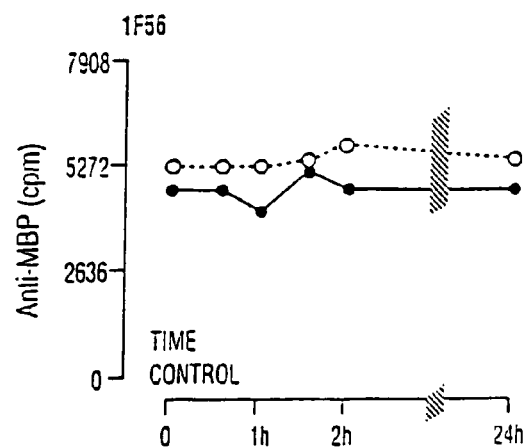
Figure 5B:
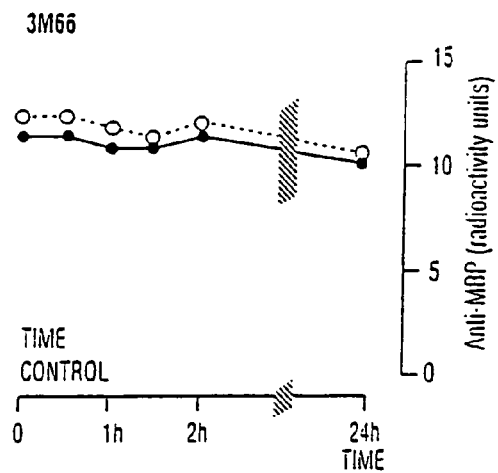

In order to determine that initially elevated CSF anti-MBP levels remained relatively constant over 24 hours, 2 patients (1 F56 and 3M66) had repeated CSF sampling every 30 minutes for 2 hours as well as 24 hours later with F and B anti-MBP monitoring (FIGS. 5A and 5B, respectively). Patients 1F56 and 3M66 served as "time controls". F and B anti-MBP levels remained constantly elevated when CSF was sampled every 30 minutes for 2 hours as well as 24 hours later.

Figure 5C:
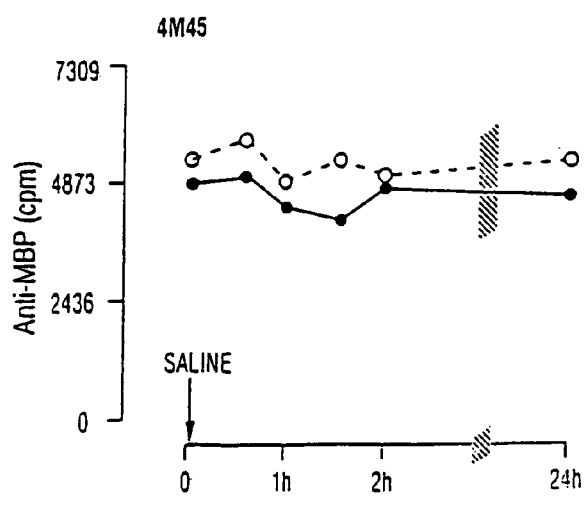
Figure 5D:
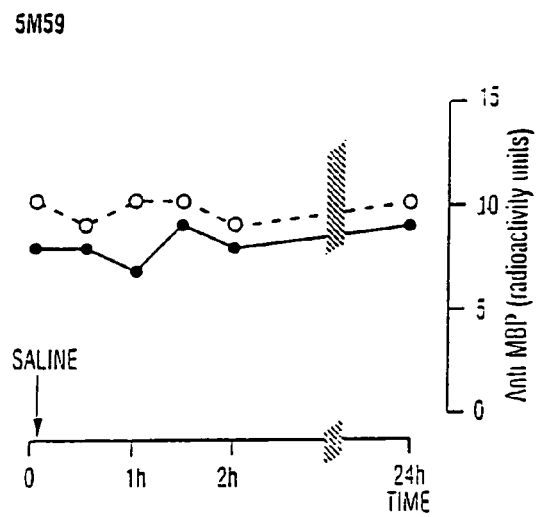
Figures 6A, 6B:
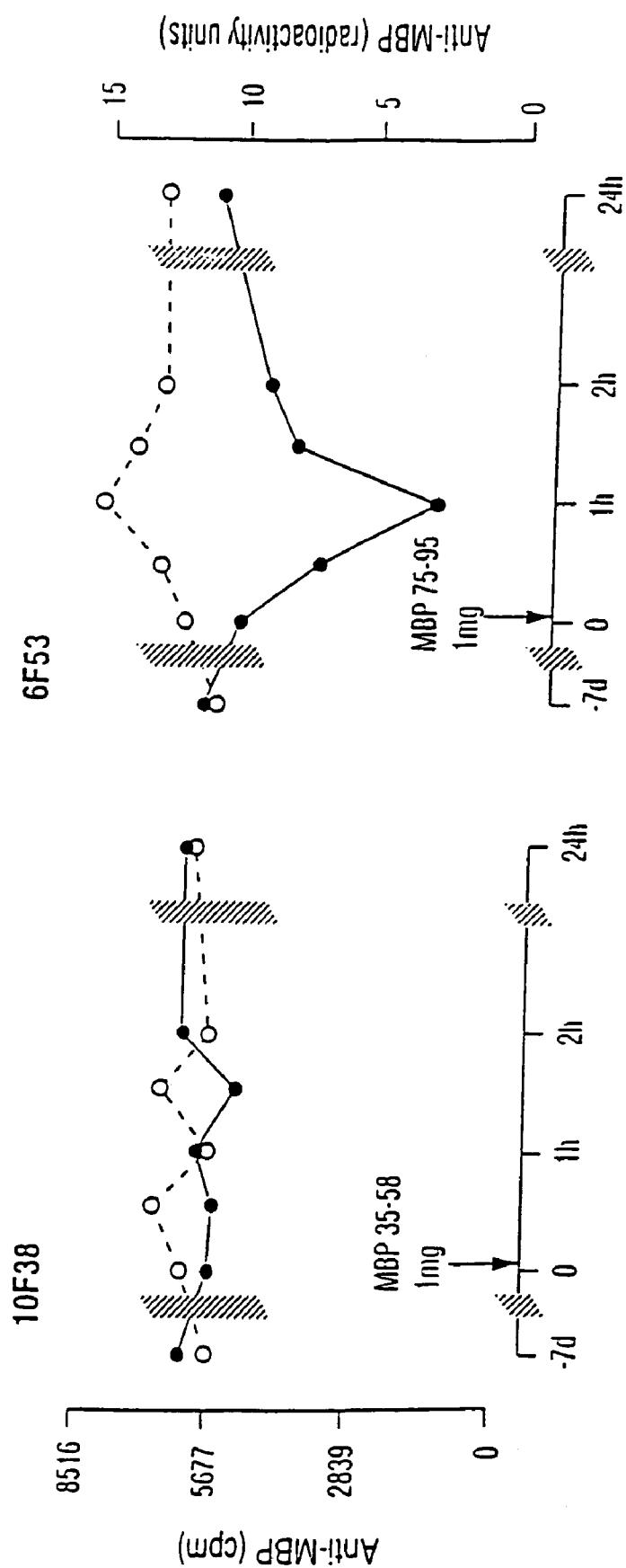
Figure 6C:
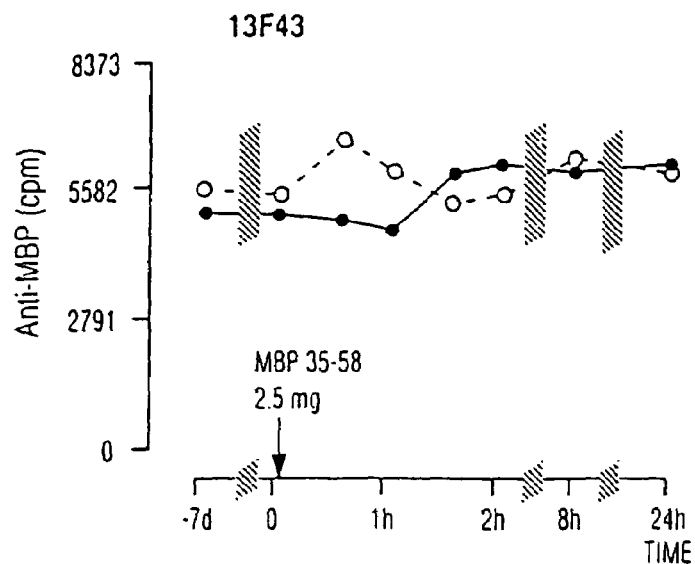
Figure 6D:
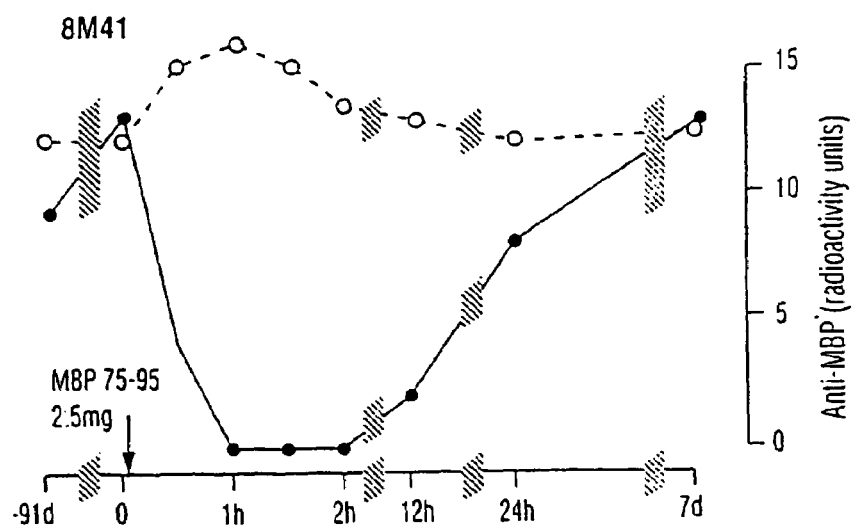
Figure 6E:
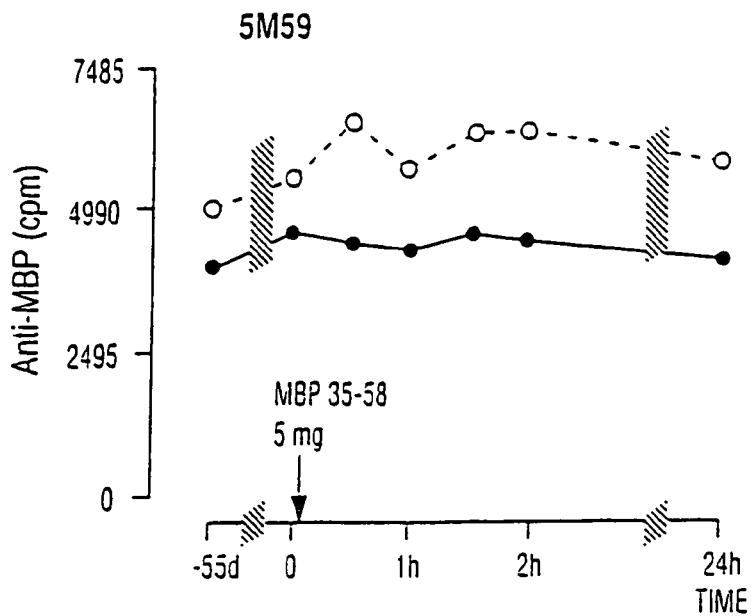
Figure 6F:
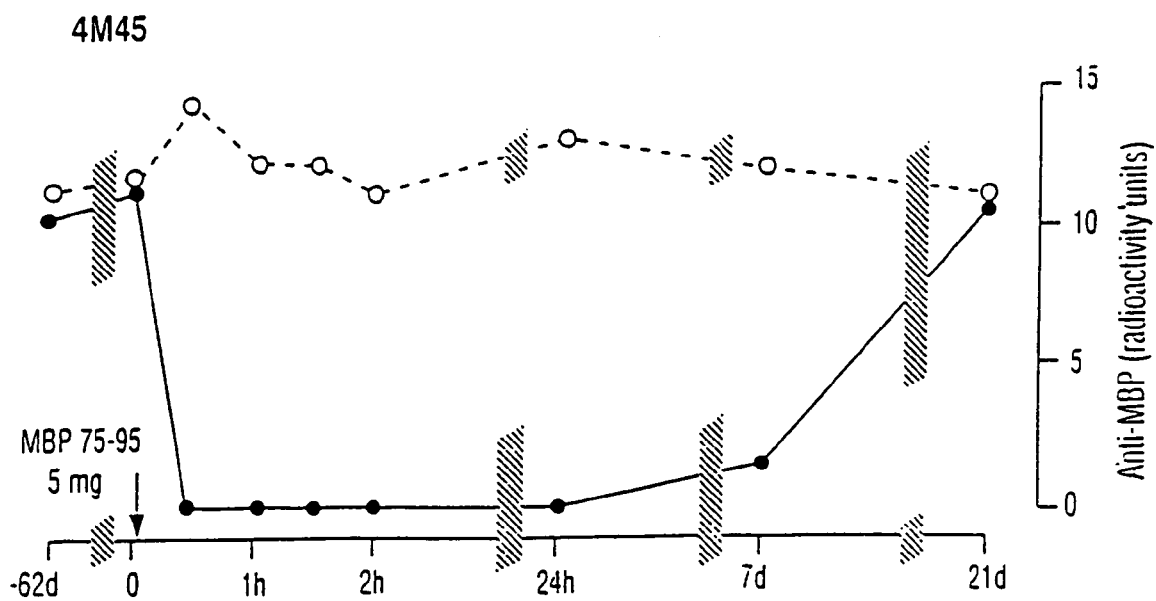
Figure 6G:
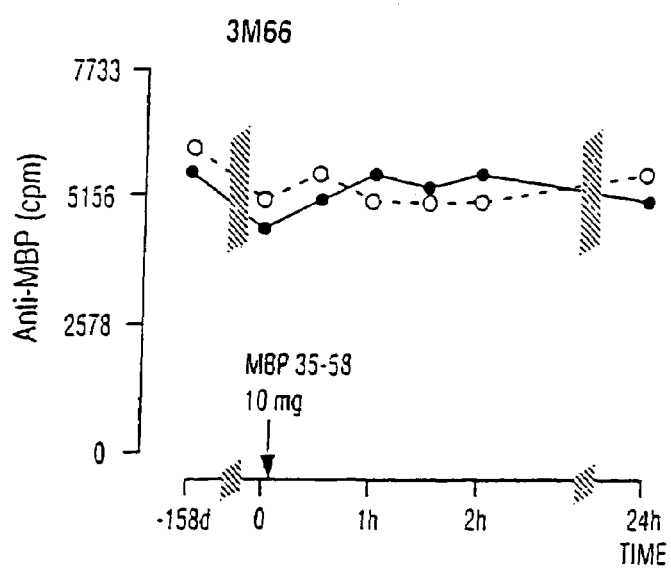
Figure 6H:
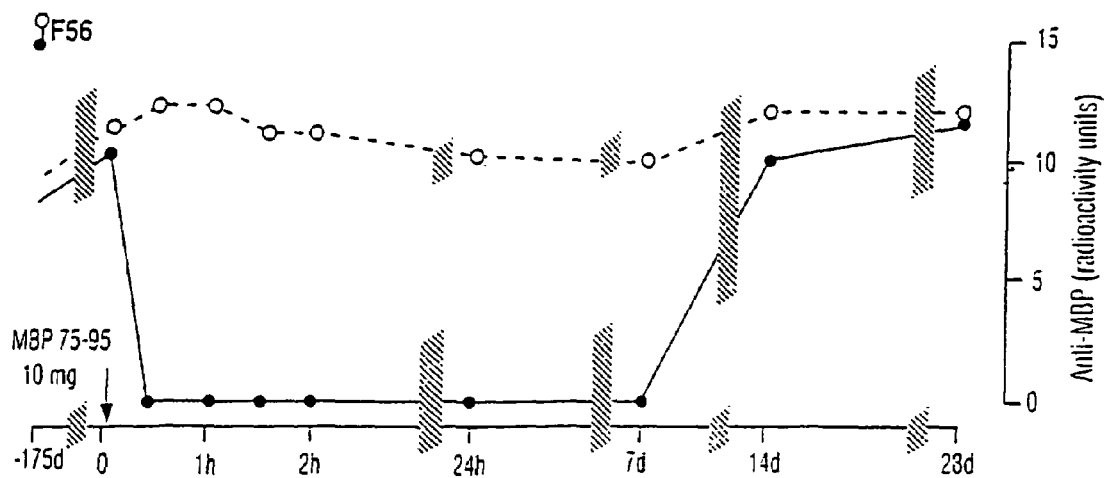
Figure 7A:
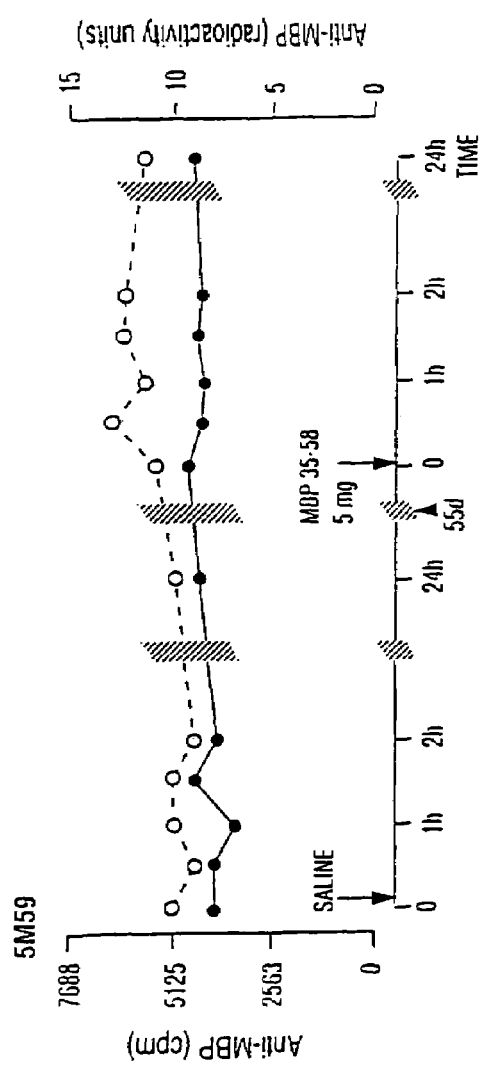
Figure 7B:
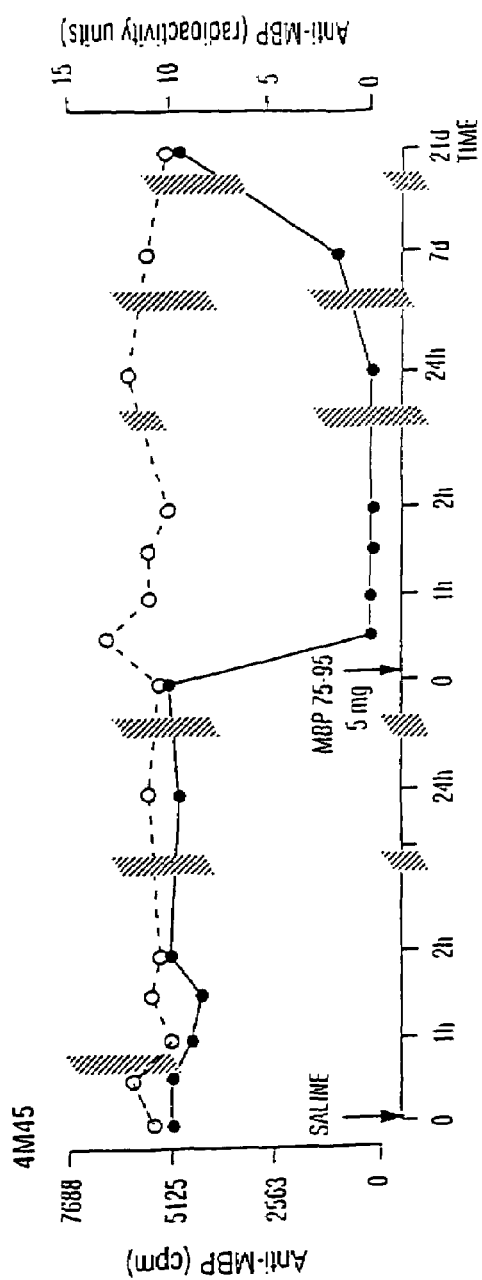
Figure 7C:
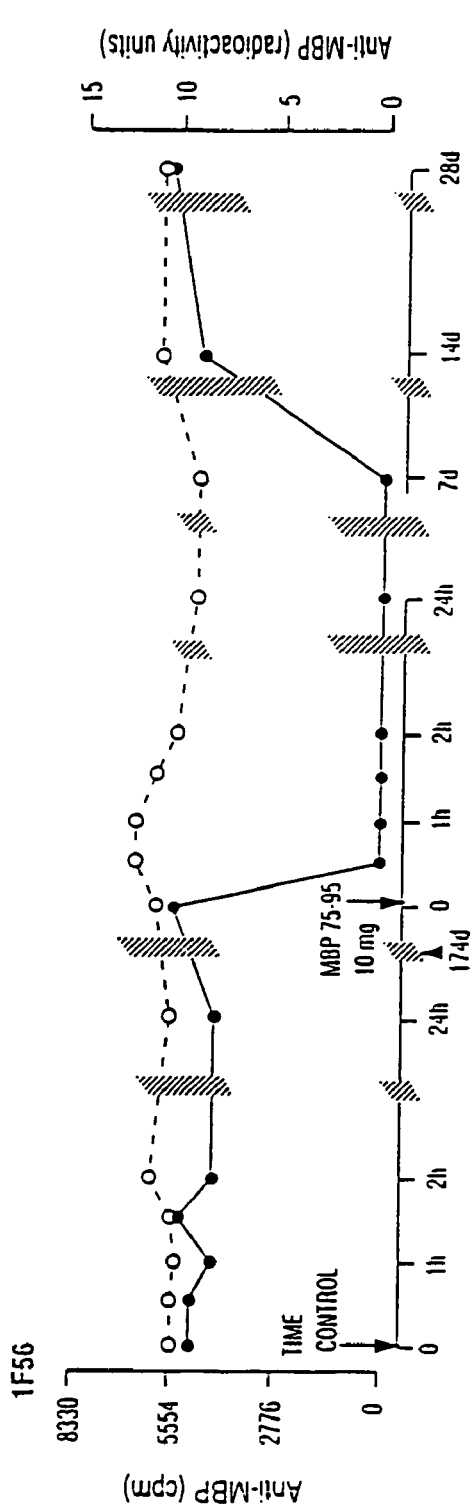
Figure 7D:
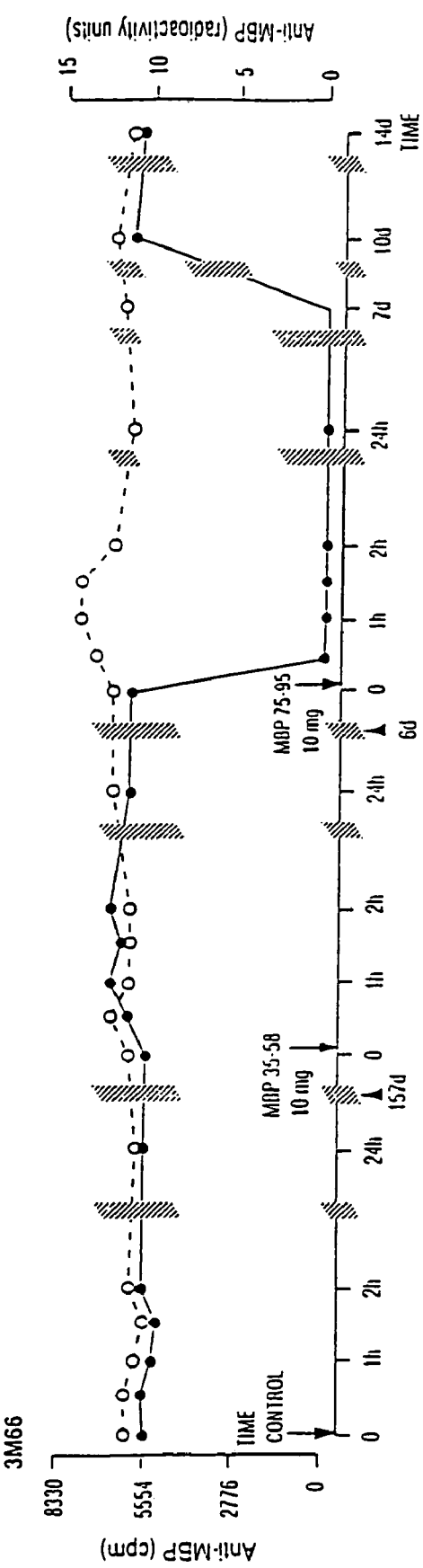

In addition the effect of inoculating 5 cc of normal saline into the CSF was similarly determined in two other patients (4M45 and 5M59; FIGS. 5C and 5D, respectively). These patients served as "time-saline controls". When 5 cc of normal saline were injected intrathecally, F and B anti-MBP levels remained elevated at baseline level when CSF was sampled as above, thus demonstrating that the "dilution effect" on anti-MBP titers was negligible.

Anti-MBP levels were determined by a solid phase radioimmunoassay with human MBP coated on Immulon microtiter wells. Immulon microtiter wells were coated with 100 µl of 10 µg/ml of MBP (1 µg/well) and incubated overnight at 37° C. After quenching with bovine serum albumin (BSA) and three water washes, the wells were stored at room temperature. Samples of 100 µl of CSF or tissue extracts diluted to 0.010 gm of IgG/l (with 0.01 M Barbitol Buffered Saline (BBS) pH 6.9-7.1, 0.5% BSA and 0.05% Tween 20) were incubated in MBP-coated wells for 1-2 hours at room temperature. After 5 buffer washes (with 0.01 M BBS, 0.5 BSA and 0.05% Tween 20), wells were incubated with goat anti-rabbit IgG-Fc specific (in 0.01 M BBS, 0.05% Tween 20, 0.5% BSA) for 1 hour at room temperature and then rinsed as above. Finally, $^{125}$I-protein A (or $^{125}$I-protein G) was added and incubated for 1 hour at room temperature. When $^{125}$I-protein G was used as a tracer, ovalbumin replaced BSA in assay buffer and for quenching. After three final water washes wells were individually counted. Results are expressed in radioactivity defined as: (counts of sample−counts of blank)÷(counts of total radioactivity−counts of blank). All samples are run in 10 replicate and counting time is 10 minutes in order to collect>10,000 counts for any positive sample.

Prior to being assayed all CSF and/or tissue samples were diluted to a final IgG concentration of 0.010 g/l. F anti-MBP was detected directly in CSF or tissue extract while B levels of antibody were determined following acid hydrolysis of immune complexes with glycine HCl buffer pH 2.2. Non-specific binding was performed for each sample in uncoated wells. For epitope localization, synthetic peptides were firstly reacted with purified antibody in a liquid phase competitive assay and then anti-MBP was determined by radioimmunoassay in all resulting supernatants. Results of the combined competitive binding assay and radioimmunoassay were expressed as percent inhibition of synthetic peptide defined as 100—radioactivity units. Samples were done in 10 replicates and counted for 10 minutes each in a LKB1275 Minigamma counter. A pool of tissue-purified anti-MBP was used at 5 pre-established dilutions as positive controls. Pooled CSF from patients with non-neurological diseases was used as negative controls. Within assay reproducibility was between 3 and 5% and between assay variation was less than 7%.

Persistence of CSF anti-MBP at an elevated and constant level in patients who participates as controls (time control and diluent control) permitted the next step of this research.

Double Blind Peptide Controlled Phase 1 Experiment—Intrathecal Injection

A Phase 1 experiment to determine the effect of synthetic peptide MBP75-95 on F and B titers of CSF anti-MBP was conducted. Subsequent to receiving approval from the Research Ethics Board of the University of Alberta, this project was conducted in patients with clinically definite MS (Schumacher et al., Ann. N. Y. Acad. Sci., 122, 552-568 1965), severely disabled and with advanced progressive disease. After obtaining informed consent, 14 patients volunteered for this study; eight patients were selected on the basis of their initial titre of F CSF anti-MBP (above 8 radioactivity units) (Table 2) to receive one intrathecal injection of either peptide MBP75-95 which bound anti-MBP in vitro or a non-binding control peptide MBP35-58 (Warren and Catz, 1993b). The experiment was conducted in a double blind fashion so that neither the researchers nor the patients had knowledge of the nature of the inoculum. All peptides were coded with 7 digit randomly generated numbers by an independent physician. Paired peptides dissolved in 5 cc normal saline and injected into the CSF by means of a lumbar puncture were administered in increasing dosages of 1, 2.5, 5 and 10 mg. CSF was sampled prior to injection (baseline), at 30 minute intervals for 2 hours after injection, 24 hours later and then at weekly intervals for 3-4 weeks until anti-MBP levels returned to baseline. Cell counts, total protein, glucose, IgG and albumin levels were determined in all CSF samples obtained. F and B anti-MBP levels were determined by radioimmunoassay, as described above.

TABLE 2

| Patient ID #, sex, age | Disease duration (years) | Kurtzke EDSS | CSF anti-MBP (radioactivity units) Free(F) | Bound(B) | Selected for research |
|---|---|---|---|---|---|
| 1F56 | 10 | 8.5 - Triplegia | 9 | 10 | Yes |
| 2M50 | 18 | 6 - Paraparesis | 2 | 10 | No |
| 3M66 | 20 | 9 - Quadriplegia | 11 | 12 | Yes |
| 4M45 | 21 | 9 - Quadriplegia | 10 | 11 | Yes |
| 5M59 | 28 | 9 - Quadriplegia | 8 | 10 | Yes |
| 6F53 | 19 | 9 - Quadriplegia | 10 | 9 | Yes |
| 7F33 | 11 | 6 - Paraparesis, ataxia | 5 | 13 | No |
| 8M41 | 8 | 8 - Triplegia | 9 | 12 | Yes |
| 9M49 | 7 | 7 - Paraparesis | 5 | 10 | No |
| 10F38 | 7 | 8.5 - Paraplegia | 11 | 10 | Yes |
| 11M49 | 20 | 8 - Triplegia | 6 | 13 | No |
| 12M35 | 12 | 6.5 - Paraparesis, ataxia | 7 | 12 | No |
| 13F43 | 15 | 8 - Paraplegia | 9 | 10 | Yes |
| 14F32 | 4 | 6 - Paraparesis, ataxia | 8 | 7 | No |

Table 2: Clinical data and CSF anti-MBP levels of 14 patients with chronic progressive MS who volunteered to participate in a Phase 1 research study of one intrathecal injection of MBP synthetic peptides. Since an initially high F anti-MBP (>8 radioactivity units) was necessary in order to achieve a significant post injection change, only 8 of 14 patients were selected for the study.

All peptides used in these studies were synthesized under the "good manufacturing product" (GMP) code using the Fmoc (9 fluorenylmethoxycarbonyl) method by Procyon Inc. (London, Ontario, Canada). Peptide purity was checked by reverse phase high pressure liquid chromatography with a C18 column and water-acetonitrile gradient containing 0.1% TFA. Mass spectroscopy and aminoacid analysis were performed by standard methods. Prior to inoculation all peptides were checked for pyrogenicity (Vancouver General Hospital, Vancouver, Canada), sterility (Provincial Laboratory for Public Health for Northern Alberta, Edmonton, Canada) and acute toxicity (Health Sciences Laboratory Animal Services, University of Alberta, Edmonton, Canada) and they were declared "suitable for administration to humans". Appropriate amounts of coded synthetic peptides were dissolved in 5 cc of sterile normal saline (0.9% sodium chloride injection USP, nonpyrogenic, Baxter Corp, Toronto, Canada), filtered two times through 0.22 µm sterilizing filter units (Millex-GX, Millipore Corp., Bedford, Mass., USA) and administered into the CSF by means of a lumbar puncture.

Interpatient Peptide Studies

Patients 6F53, 8M41, 4M45 and 1F56 received synthetic peptide MBP75-95 capable of binding anti-MBP in vitro and patients 10F36, 13F43, 5M59 and 3M66 received a "control", non-binding synthetic peptide MBP35-58 in increasing amounts of 1, 2.5, 5 and 10 mg respectively (FIG. 6). In patient 6F53 (FIG. 6B) who received 1 mg MBP75-95 a 75% decrease of F anti-MBP followed by its immediate return to baseline level was observed; patient 8M41 (FIG. 6D) who received 2.5 mg MBP75-95 showed complete binding-neutralization of F anti-MBP followed by its return to baseline level within 24 hours; in patient 4M45 (FIG. 6F) who received 5 mg MBP75-95, a precipitous and complete F anti-MBP binding-neutralization occurred and persisted for 7 days, having returned to its initial value when sampled 21 days later; patient 1F56 (FIG. 6H) received 10 mg MBP75-95 which also produced complete binding-neutralization of F anti-MBP which persisted for 7 days and had returned to baseline value when sampled 14 and 28 days later. Bound levels of anti-MBP were not significantly altered by one intrathecal inoculation of MBP75-95. In patients 10F38, 13F43, 5M59 and 3M66 who received respectively 1, 2.5, 5 and 10 mg of the "control" non-binding peptide MBP35-58, F and B levels of CSF anti-MBP remained unchanged from initially high baseline levels during the 24 hour experiment (FIGS. 6A, 6C, 6E and 6G, respectively). Traditional CSF parameters of inflammation in MS, such as cell counts, absolute levels of total protein, IgG and albumin, oligoclonal banding, IgG index and CNS IgG synthesis remained unchanged prior to and after peptide administration.

Intrapatient Peptide Studies

Intrapatient experiments were conducted in order to minimize interpatient variability. In patient 5M59 who was either a "time-control" or received 5 ml of the non-binding peptide MBP35-58, F anti-MBP levels remained elevated at baseline level during both experiments (FIG. 7A). Patient 4M45 was initially a "diluent control" and two months later he received 5 mg MBP75-95. His F anti-MBP remained constantly elevated in all samples collected during the "diluent" experiment, and it became undetectable after administration of MBP75-95 (FIG. 7B). Similar results were obtained in patient 1F56 who had persistently elevated levels of F antibody during a "time control" experiment and after administration of 10 mg MBP75-95 her F anti-MBP became undetectable (FIG. 7C). A complete study was performed in patient 3M66. His F anti-MBP levels were persistently elevated during a "time control" experiment or when 10 mg MBP35-58 were administered; however, when 10 mg MBP75-95 were injected, F anti-MBP was completely neutralized and remained undetectable for 7 days (FIG. 7D).

Repeated Administration of Synthetic Peptide MBP75-95

After determining that peptide MBP75-95 neutralized F anti-MBP in vivo for periods in excess of 7 days, it was elected to repeatedly inoculate 10 mg MBP75-95 into the spinal fluid at weekly intervals for 10 weeks. This experiment was conducted, in 3 different patients with chronic progressive MS who have not participated in the single peptide injection project and volunteered for this study. F and B anti-MBP were determined 1-2 weeks prior to the first inoculation, prior to and 30 minutes following each of the 10 injections and again 1 month after the last injection. Cell counts, total protein, glucose, IgG and albumin levels were determined in all CSFs obtained before each of the 10 injections. Prior to the first and after the last injection blood was obtained and analyzed for electrolytes, creatinine, cardiac and liver enzymes and hematology panel.

When MS patients with chronic progressive disease received repeated intrathecal injections of 10 mg MBP75-95 at weekly intervals, for periods up to 10 weeks, their initially high F anti-MBP was undetectable for as long as the peptide was administered; when the peptide was no longer administered, F anti-MBP returned to baseline level within 1 month (FIG. 8). Titers of B antibody remained constantly elevated throughout the experiment suggesting that in these patients synthesis of anti-MBP continued and intrathecal peptide administration produced only a "mopping effect" of F anti-MBP.

Patients who received either a single synthetic peptide injection or repeated weekly injections had chronic progressive multiple sclerosis with an advanced degree of neurological disability. None of these patients reported worsening of their neurological symptoms or MS exacerbations subsequent to intrathecal peptide administration and a cellular response did not develop in CSF. MS patients receiving repeated inoculations of MBP75-95 have been monitored for systemic complications including electrolyte changes as well as cardiac-liver-kidney dysfunction and hematology changes and no adverse complications have occurred. No adverse effects were observed.

Intravenous Administration of MBP75-95

Subsequent to determining that intrathecal administration of peptide MBP75-95 produced complete binding-neutralization of F anti-MBP with no change in levels of B antibody, it was decided to determine the effect of intravenous administration of the same peptide on CSF titers of F and B anti-MBP; 500 mg of MBP75-95 were dissolved in 100 cc of normal saline and injected intravenously over 30 minutes into patient 8M41 with CSF anti-MBP monitoring every 30 minutes for the first two hours, 18 hours later as well as 10, 16 and 30 days later. Blood was obtained before injection as well as 16 and 30 days later and analyzed for electrolytes, creatinine, cardiac and liver enzymes and hematology panel. Spinal fluid was monitored for cell counts, total protein, glucose, IgG and albumin levels. No adverse effects were observed.

As shown in FIG. 8, intravenous administration of 500 mg MBP75-95 did not produce any change in titers of F and B levels of CSF anti-MBP within the first two hours. A 30% decline in CSF F anti-MBP was observed 18 hours later. When CSF was resampled 10, 16 and 30 days later both F and B anti-MBP had declined from their initial level of 11 radioactivity units to 4, 2, and 1 radioactivity units respectively.

A repeated observation in all patients treated intrathecally with MBP 75-95 was the persistence of elevated levels of bound antibody, while F anti-MBP became undetectable in a dose-response fashion. This suggested that synthesis of autoantibodies to MBP remained active during and subsequent to intrathecal administration of MBP75-95. As a consequence of this observation, MBP75-95 was administered intravenously to a patient who had previously received a single intrathecal injection of the peptide. After intravenous administration both F and B levels of CSF anti-MBP showed a significant decline when monitored for periods up to one month. The decline of F as well as B levels of CSF anti-MBP subsequent to intravenous administration of MBP75-95 suggests that this route of administration produced downregulation of the autoimmune inflammatory process responsible for the synthesis of anti-MBP. In a follow-up study to date anti-MBP levels started to increase 4-6 months after a first intravenous injection; a second intravenous injection of the same peptide (booster) produced down regulation of anti-MBP synthesis for up to 2 years in approximately 70 different patients with chronic progressive MS.

MBP Epitope for MS Anti-MBP

In order to further localize the MBP epitope for MS anti-MBP, F and B anti-MBP purified by affinity chromatography from CSF and MS brain tissue (Warren, K. G. et al., Ann. Neurol. 35, 280-289, 1994) were reacted in competitive inhibition assays with 41 consecutive MBP synthetic peptides of equal length (each of 10 residues and overlapping the adjacent ones by 9) covering the area between residues 61 and 110 of human MBP. The peptide(s) producing maximum inhibition were considered to be most highly associated with the antibody binding site.

Maximum inhibition (≧80%) of both purified F and B anti-MBP from MS brain tissue (FIG. 10) was produced by four decapeptides namely MBP84-93, MBP85-94, MBP86-95 and MBP87-96 suggesting that the MBP epitope for MS anti-MBP is located between residues 84 and 96. The minimum area of common amino acid residues is from residue 87 to residue 93. B anti-MBP had a more restricted range than F antibody.

The role of anti-MBP antibodies in the pathogenesis of MS demyelination has not been elucidated and can only be determined by modulating anti-MBP in vivo and subsequently observing the clinical and pathological outcomes. For example, during an acute relapse of MS, when F/B antibody ratios are above unity a peptide known to bind F anti-MBP could be inoculated intrathecally, in order to bind free circulating antibody and terminate the clinical effects of the acute relapse; weekly administration may be required until remission occurs. In MS patients with chronic progressive disease and superimposed acute relapses, intrathecal as well as intravenous peptide administration may be required in order to down regulate inflammatory mechanisms which produce anti-MBP.

EXAMPLE 3

Appropriate Dosage of Intrathecally Administered pMBP86-95 or pMBP82-98 in Acute Relapsing Patients MS relapses are associated with F/B anti-MBP ratios greater than 1.0 due to higher levels of free than bound antibody in CSF. Generally, over a period of 3 months, as a relapse enters into the subsequent recovery/remission phase, F anti-MBP levels gradually decline, and when biological remission is complete, CSF, F and B anti-MBP generally become undetectable in CSF.

Patients who participated in the following Examples had either relapsing-remitting or relapsing-progressive MS.

In this and the following Examples either pMBP86-95 or pMBP82-98 were used. pMBP86-95 had very low solubility in normal saline since it contained four hydrophilic and six hydrophobic residues. On the other hand, pMBP82-98 has increased solubility in normal saline, as a result of the five additional hydrophilic residues.

Two patients were studied to determine the appropriate dosage of intrathecally administered pMBP86-95 or pMBP82-98, which will reduce immediately the F anti-MBP to undetectable levels. One patient had an acute relapse of gait ataxia and truncal dysequilibrium. At the onset of the attack, this patient received a single intrathecal injection of 10 mg pMBP86-95; F and B anti-MBP levels were measured before and 1 hour after injection and five more times during the next 3 months. This dosage suppressed F anti-MBP only partially and the antibody recovery curve followed closely the natural course; this patient continued to have progressive spastic paraparesis and ataxia. It was concluded that a single intrathecal injection of 10 mg pMBP86-95 was inadequate to fully suppress F anti-MBP and alter its natural recovery rate.

The other patient, an 18 year old female, with acute optic neuritis who received a single intrathecal injection of 50 mg pMBP86-95, had F and B antibody levels measured before and 30 minutes after injection. Thirty minutes after injection F antibody became undetectable. The patient would not agree to subsequent lumbar punctures. It was thus concluded that dosages of at least 50 mg are required to bind and neutralize F anti-MBP in CSF for at least 30 minutes.

EXAMPLE 4

Frequency and Duration of Administration in Patients with Monosymptomatic Relapses In this example the frequency and duration of administration of pMBP that would maintain low or undetectable F antibody levels for a longer time period were determined. The four patients studied in this group received synthetic peptides within a week from the onset of an attack.

The first two patients had attacks of acute unilateral optic neuritis. One of these patients (FIG. 11a) received intrathecally two injections of 50 mg pMBP86-95 (it#1, it#2) four weeks apart. After each injection F anti-MBP became undetectable within 1 h. When measured 1 week after the first injection the F anti-MBP was elevated, and 4 weeks later the F antibody was significantly high. At that time the patient has a second intrathecal injection (it#2) and F anti-MBP became undetectable after 30 minutes but it was not subsequently monitored beyond 24 hours. It was concluded that this frequency was inadequate and that multiple injections during the first week of an attack might be required to maintain negligible antibody levels.

The second patient with complete unilateral optic neuritis received multiple intrathecal peptide injections of 50 mg pMBP82-98 during the first week of his attack: four daily injections (FIG. 11b: it#1, it#2, it#3, it#4) and a fifth injection (it#5) one week later. The anti-MBP profile of this patient showed a steady, rapid decline over the 7-day period. More important, 7 weeks and 6 months after it#5, his CSF anti-MBP levels remained undetectable and the patient did not experience a recurrence of optic neuritis nor any other type of MS relapse. In addition the unilateral blindness secondary to optic neuritis recovered fully.

The same schedule of daily intrathecal injections of 50 mg pMBP82-98 was then administered to MS patients with different types of mono-symptomatic relapses. FIG. 11c illustrates the anti-MBP profile of a patient with acute pseudoathetosis of his left hand, who received intrathecally five daily injections of 50 mg pMBP82-98 (it#1, it#2, it#3, it#4, it#5) in the second week of his attack. F anti-body levels declined to undetectable values within 4 days and remained undetectable when assessed 11 days and one month later. This patient steadily regained function of his left hand so he could again ride his motorcycle and play the guitar.

The last patient had an attack of acute left hemiplegia superimposed on chronic progressive MS. He had four intrathecal injections of 50 mg of pMBP86-95 every 2 to 3 days. Anti-MBP was measured before and 30 minutes after each injection (FIG. 11d: it#1, it#2, it#3, it#4) and 10 days after the first injection. The initially elevated F anti-MBP became undetectable within 7 days when the patient returned clinically and biochemically to his initial chronic progressive state, and soon afterwards he received intravenously 400 mg pMBP86-95. This suppressed his bound antibody level for 4 months after the i.v. injection. However, after his last lumbar puncture at 8.5 months post intravenous injection, the disease had returned to chronic progressive pattern both clinically and biochemically.

EXAMPLE 5

Frequency and Duration of Administration in Patients with Polysymptomatic Relapses The same MBP peptides were then injected in patients with polysymptomatic attacks, affecting multiple areas of the CNS. This group consisted of three patients: one with relapsing-remitting and two with relapsing-progressive disease.

The first patient had a severe polysymptomatic exacerbation. During the first week of the relapse she received three injections of 50 mg pMBP86-95 on days 1, 3 and 7 (FIG. 12: it#1, it#2 and it#3). Anti-MBP was measured before each injection and 30 minutes later. After receiving these three injections F anti-MBP was suppressed to almost undetectable levels. When measured a month later, F anti-MBP was rising and by 1.5 months, the relapse was once again clinically active and biochemically confirmed. At that time the patient received a second course of four intrathecal injections of 50 mg pMBP86-95 on days 45, 48, 49, and 50 of the relapse (it #4, it#5, it#6 and it#7). Anti-MBP was measured before and thirty minutes after each injection and three more times in the subsequent two months. Once again F anti-MBP was suppressed for at least two weeks, but the patient relapsed again, and at that time her F antibody level had returned to the initial pre-relapse level. Clearly a more sustained intrathecal administration of the synthetic peptide, in order to maintain low/undetectable levels of F anti-MBP for longer periods of time is required.

The second patient had relapsing-progressive MS (FIG. 13). Initially in the progressive form (F=B), he received intravenously 500 mg pMBP86-95 (IV #1). Although both F and B antibody levels were somewhat decreased after one month, 9 weeks after the I.V. injection, the patient experienced a polysymptomatic clinical relapse associated with a highly increased F anti-MBP level. At this time, he received three intrathecal injections of 50 mg pMBP86-95 (it#1, it#2 and it#3) at days 1, 3 and 12 of the relapse, and anti-MBP was measured before, 30 minutes and 24 hours after the first and third injection. When examined one month later, the patient had returned to his initial clinical and biochemical status of progressive spastic paraparesis when, within 2 weeks, he received a second intravenous injection of 500 mg pMBP86-95 (IV#2). To date F and B CSF anti-MBP levels monitored serially for the next 26 months remained suppressed when compared to baseline levels. His ability to stand and walk improved substantially.

The last patient in this group with MS, initially in the progressive phase (F=B), (FIG. 14), received intravenously 500 mg pMBP86-95 (IV#1). CSF anti-MBP was measured after 9 days, then monthly for 2 months and 4.5 months after IV#1. Following this injection, F and B anti-MBP levels were suppressed for 2 months; 4.5 months after IV#1, the patient was complaining of increasing weakness, confirmed clinically as well as biochemically by increased antibody levels compatible with chronic progressive disease. Within the next month he received a second intravenous injection of 500 mg pMBP82-98 (IV#2). CSF analysis of the sample taken just before the second injection, was suggestive of an acute relapse pattern (F>B), and the next day, the patient developed acute diplopia due to a left lateral rectus paresis. At this time he was clearly experiencing a clinical and biochemical acute relapse, which persisted over the next 4.5 months and was characterized by severe dysequilibrium of stance and gait, weakness of his legs and double vision. In an effort to lower his elevated F anti-MBP, this patient received intrathecally two courses of pMBP 82-98. During the first course initiated 4.5 months from the beginning of the relapse, he received 50 mg pMBP82-98, daily for 5 days (it#1, it#2, it#3, it#4 and it#5) and anti-MBP levels measured before and 30 minutes after each injection remained reasonably elevated. Since the relapse persisted and was severely disabling, it was decided to further administer a second course of a higher dosage of peptide and with a higher frequency, and the patient received 100 mg pMBP82-98 two times daily for two days (day 19 and 20: it#6, it#7, it#8 and it#9). Anti-MBP was measured before and 30 minutes after each injection. Subsequent to this increased dosage and frequency, F anti-MBP was suppressed to negligible levels, and when tested a week later (day 28) his CSF profile was compatible with slowly progressing disease (F/B anti-MBP=1.0). At this time the patient received a third intravenous injection of 500 mg pMBP 82-98 (IV#3) which did not down regulate any more anti-MBP production.

EXAMPLE 6

Intravenous Administration of MBP Peptides in an Attempt to Prevent Future Relapses Two patients with relapsing-progressive MS, who had frequent relapses were injected intravenously, with either pMBP86-95 or pMBP82-98 to determine if this route of administration will prevent further attacks.

The first patient was experiencing 2 to 3 relapses per year for 4 years, with resulting stepwise progression of spastic paraparesis (FIG. 15). She received two intravenous injections 6 months apart, one of 400 mg pMBP86-95 (IV#1) and the second of 400 mg. pMBP82-98 (IV#2); clinical monitoring and CSF analysis were performed monthly. FIG. 15 shows anti-MBP levels over a period of 9 months (upper boxed area). The first intravenous injection down regulated anti-MBP synthesis for about 2 months. During the third month post injection, this patient experienced a clinical relapse; unfortunately CSF was not obtained at that time. During the subsequent 2 to 3 months, after the relapse resolved that the illness reentered the chronic progressive phase, this patient received the second intravenous injection (IV#2). CSF anti-MBP levels were again suppressed for 2 months but, three months after the second injection, the patient had another relapse associated with markedly elevated F anti-MBP. Similar to the relapse rate she had in the previous 4 years, this patient continued to experience 2 to 3 relapses per year despite receiving two intravenous injections of pMBP86-95 and pMBP82-98.

A second patient (FIG. 16) who experienced 1 to 4 acute relapses per year for the previous 10 years (upper scale) became seriously disabled, paraplegic and confined to a wheelchair. During the 11th year the patient once again experienced four relapses (upper boxed area), although receiving MBP synthetic peptides intrathecally and intravenously. During the first relapse, after receiving intrathecally two injections of 50 mg pMBP86-95 on day 1 and day 6

(it#1, it#2) her F anti-MBP level was substantially reduced; on day 6 she also received intravenously 300 mg of pMBP86-95 (IV) which subsequently suppressed both F and B antibody for the next 3 months. Four months after the intravenous injection, this patient experienced another clinical relapse which continued to worsen in time: CSF antibody levels were highly elevated, and 6.5 months after the IV injections the patient received a course of four daily injections of 50 mg pMBP82-98 (it#3, it#3, it#5 and it#6), which failed to suppress F antibody levels and to resolve the clinical relapse.

EXAMPLE 7

Comparison of Different Routes of Peptide Administration

In initial studies, synthetic MBP peptides were administered to eight chronic progressive MS patients. Patients received intrathecally either an MBP binding peptide MBP (75-95) or a control non-binding peptide MBP(35-58) in increasing doses from 1 to 10 mg in 5 ml of saline; the four patients who initially received the control non-binding peptide (MBP35-58) later received the binding MBP(75-95) peptide.

Injection of MBP(75-95) into CSF resulted in transient neutralization of F MBP specific antibodies; bound MBP autoantibodies were not affected. The duration of the effect lasted 1 hour (1 mg of peptide), 24 hours (2.5 mg of peptide) or 7 days (5-10 mg of peptide). Since the effect of intrathecal peptide administration was incomplete (B anti-MBP remained elevated) and relatively short-lived, this route of administration was compared to intravenous injection. In contrast to intrathecal administration, both free and bound MBP autoantibodies became undetectable one month after a single intravenous injection of 500 mg of MBP(75-95) and remained at low levels for three months and after a booster injection for up to 26 months (FIG. 17). Similar observations were made to date in approximately 70 patients with chronic progressive MS who were injected intravenously with an MBP binding peptide such as MBP75-95, MBP86-95, MBP82-98. A dose of 500 mg (5 mg/kg bodyweight) in 10-50 ml of normal saline, was chosen because of the larger volume of blood versus CSF (factor 15) and the rapid clearance of peptides from the bloodstream through the kidney; peptide doses corresponding to those given intravenously were not administered intrathecally because such volumes could not be injected into CSF. In summary, intrathecal administration, in the dose range tested in these patients, resulted in a transient "mopping" of F anti-MBP only, in contrast to intravenous injection(s) that down regulated anti-MBP synthesis, a single intravenous injection induced long-lasting tolerance.

EXAMPLE 8

Duration of Tolerance Following Intravenous Administration of the MBP Peptide

Based on these results, kinetics of tolerance to MBP were examined to date in approximately 70 patients with chronic-progressive MS who were followed for over two years following multiple intravenous injections of MBP(75-95), MBP(86-95) or MBP(82-98). Peptides were dosed at 5-6 mg/kg body weight (256-500 mg) and injected intravenously in 10-50 ml of saline. Prior to intravenous peptide administration, all 13 patients had high levels of free and bound MBP antibodies in CSF (FIG. 18, Table 3). One month following peptide administration, MBP specific antibodies became essentially undetectable and remained at low levels generally for 3-4 months, at which time antibody levels began to rise again; some returning to their initial levels by 8 months. Six to ten months following IV#1, all patients received a booster injection (IV#2) of 275-500 mg (5-6 mg/kg body weight) of MBP(82-98) in 10 ml of saline (IV#2). The longer peptide chosen for the second injection was more soluble and could be dissolved and administered in a smaller volume. In this group as a whole, CSF anti-MBP levels declined dramatically within 6 weeks to 2 months from the injection and remained undetectable for a longer time (up to 26 months). Of the whole group of approximately 70 patients, one was unable to complete the study due to a pulmonary embolus and subsequent anticoagulant therapy that prevented further lumbar punctures, and another was excluded from follow-up because of receiving high dose intravenous corticosteroids. Individually, of the approximately 70 patients, about 63 had undetectable anti-MBP levels, 18-26 months after the booster injection.

EXAMPLE 9

Long-lived Tolerance in Patients with the HLA-DR2 Haplotype

The HLA-DR haplotypes of MS patients were determined by molecular typing of genomic DNA (Table 3). Four of eleven patients who completed the study carried the disease associated DR2 haplotype (DRB1*1501 or DRB1*15021); all of these patients had low or undetectable autoantibodies levels one year following the second intravenous MBP peptide injection. The MBP peptide binds with high affinity to HLA-DR2 and is immunodominant for HLA-DR2 restricted, MBP specific T cells. HLA-DR4 (DRB1*0401) and HLA-DR7 (DRB1*0701) bind the MBP peptide that was administered; binding studies have not been done for the DR molecules carried by patient k(M) (DRB1*0407, DRB1*0801). The MBP peptide is not bound by HLA-DR3 (DRB1*03011); two patients who had elevated anti-MBP at the end of the study carried the DRB1*03011 haplotype (Table 3). These data indicate that the duration of tolerance to MBP depends on the HLA-DR haplotype of a patient. Tolerance may be more long-lived when both MBP specific T cells and B cells are tolerized.

TABLE 3

HLA-DR haplotypes of MS patients

| Patient | HLA-DR Haplotypes | Total Anti-MBP (Ru) |
|---|---|---|
| A. Low levels of total anti-MBP at 1 year following IV#2 | | |
| b (F) | DRB1*1501 | 4.1 |
| e (F) | DRB1*1501 DRB1*1303 | 2.5 |
| m (M) | DRB1*1501 DRB1*0101 | 3.9 |
| 1 (F) | DRB1*15021 DRB1*0403 | 3.9 |
| a (M) | DRB1*1401 DRB1*0701 | 4.1 |
| f (F) | DRB1*0701 | 2.4 |
| k (M) | DRB1*0407 DRB1*0801 | 4.5 |
| B. Elevated levels of total anti-MBP at 1 year following IV#2 | | |
| j (M) | DRB1*03011 | 7.3 |
| h (F) | DRB1*0101 DRB1*0701 | 9.7 |
| g (F) | DRB1*0101 DRB1*1101 | 19.1 |
| I (M) | DRB1*0403 DRB1*03011 | 19.0 |

TABLE 3-continued

HLA-DR haplotypes of MS patients

| Patient | HLA-DR Haplotypes | Total Anti-MBP (Ru) |
|---|---|---| total anti-MBP: free anti-MBP + bound anti-MBP
HLA-DR haplotypes of 11 MS patients who completed the 1 year follow up form the second intravenous peptide injection (IV#2). All four patients with HLA-DR2 haplotype (DRB1*1501 or DRB1*15021) had low autoantibody levels one year following IV#2.

EXAMPLE 10

Subcutaneous Peptide Administration Does Not Induce Tolerance

The optimal route of peptide administration was further investigated by subcutaneous injection(s) of MBP(82-98) in saline in a group of 33 MS patients. In 26 MS patients, increasing amounts (1 to 100 mg) of a single subcutaneous injection of MBP(82-98) did not affect CSF autoantibody levels to MBP (data not shown); eight of these patients subsequently received an intravenous peptide injection and within two months CSF antibody levels became undetectable (Table 4A). In five other patients, a total dose of 900-1000 mg (5×100 mg, daily for five consecutive days, followed by another subcutaneous injection of 400 or 500 mg) only resulted in a modest decrease of MBP antibody levels in CSF (Table 4B). To examine whether a different schedule of administration would be more effective, two patients received two subcutaneous injections of 250 mg of MBP(82-98) one month apart (Table 4C). Again, autoantibody levels were not affected. Taken together, these data demonstrate that only intravenous administration of the MBP peptide induces long-lived tolerance to MBP at the peptide doses tested in this study.

TABLE 4

A

| Patient ID (sex) | MBP (82-98) SC mg | Baseline f | Baseline b | 6-7 weeks f | 6-7 weeks b | Elapsed time (months) | Baseline f | Baseline b | MBP (82-98) IV#1 mg | 2 months f | 2 months b | 4 months f | 4 months b |
|---|---|---|---|---|---|---|---|---|---|---|---|---|---|
| E(F) | 5 | 9.1 | 11.2 | 10.2 | 10.4 | 6 | 9.3 | 9.8 | 400 | 1.0 | 1.1 | 1.4 | 1.0 |
| K(F) | 7 | 2.1 | 3.4 | 3.1 | 5.9 | 6.5 | 6.3 | 6.7 | 500 | 1.5 | 0.8 | | |
| N(F) | 10 | 8.1 | 8.0 | 7.1 | 8.1 | 8 | 6.6 | 5.6 | 500 | 3.0 | 3.0* | | |
| Q(F) | 40 | 9.9 | 10.1 | 10.9 | 8.3 | 6 | 10.0 | 9.3 | 400 | 1.5 | 1.6 | 2.1 | 2.1 |
| R(M) | 50 | 10.2 | 10.3 | 11.1 | 7.4 | 6 | 7.5 | 9.9 | 500 | 1.5 | 1.6 | 1.5 | 1.7 |
| S(F) | 60 | 4.1 | 4.3 | 6.1 | 5.4 | 6.5 | 7.4 | 7.4 | 500 | 1.8 | 0.9 | | |
| X(M) | 100 | 9.9 | 7.3 | 9.5 | 8.2 | 4.5 | 9.7 | 9.0 | 500 | 1.4 | 1.0 | 1.5 | 1.1 |
| Z(M) | 100 | 9.9 | 8.4 | 10.9 | 10.1 | 4.5 | 10.5 | 9.7 | 500 | 2.0 | 1.9 | 1.5 | 1.6 |
| MEAN | | 7.9 | 7.9 | 8.6 | 8.0 | | 8.4 | 8.4 | | 1.7 | 1.5 | 1.6 | 1.5 |
| SD | | 2.9 | 2.6 | 2.7 | 1.7 | | 1.5 | 1.5 | | 0.6 | 0.7 | 0.3 | 0.4 |

B

| Patient ID (sex) | MBP (82-98) SC mg | Baseline f | Baseline b | 6-7 weeks f | 6-7 weeks b | Elapsed time (months) | MBP (82-98) SC mg | 7 weeks f | 7 weeks b |
|---|---|---|---|---|---|---|---|---|---|
| AA(F) | 100/d × 5 | 7.7 | 8.1 | 4.4 | 4.9 | 0.5 | 400 | 4.3 | 3.4 |
| BB(F) | 100/d × 5 | 5.4 | 5.4 | 3.5 | 3.7 | 0.5 | 500 | 2.0 | 2.5 |
| CC(M) | 100/d × 5 | 5.9 | 5.4 | 6.9 | 8.8 | — | — | | |
| DD(F) | 100/d × 5 | 4.6 | 4.8 | 2.7 | 1.9 | 0.5 | 500 | 3.0 | 2.8 |
| EE(F) | 100/d × 5 | 7.4 | 8.9 | 3.7 | 3.9 | 0.5 | 400 | 2.6 | 2.4 |
| MEAN | | 6.2 | 6.5 | 4.2 | 4.6 | | | 3.0 | 2.9 |
| SD | | 1.2 | 1.7 | 1.4 | 2.3 | | | 0.8 | 0.7 |

C

| Patient ID (sex) | MBP (82-98) SC mg | Baseline f | Baseline b | 15 weeks f | 15 weeks b |
|---|---|---|---|---|---|
| GG(M) | 250/m × 2 | 8.4 | 8.7 | 7.1 | 8.3 |
| FF(F) | 250/m × 2 | 4.8 | 5.3 | 5.4 | 4.2 |

A. Eight patients received a single subcutaneous injection of MBP(82-98) (5-100 mg in 1-5 ml saline) which had no effect on MBP autoantibody levels. In contrast, a single intravenous injection (400-500 mg) of the same peptide administered 4.5 to 8 months later resulted in undetectable CSF autoantibody levels.
B. Repeated subcutaneous injections of high doses of MBP(82-98) (100 mg/day for five consecutive days) had a modest effect on CSF anti-MBP levels; an additional high dose (400 or 500 mg) of MBP(82-98) administered subcutaneously two weeks after the first set of injections did not further reduce autoantibody levels.
C. Two subcutaneous injections of high doses of MBP (82-98) (2×250 mg, one month interval) had no effect on MBP autoantibodies in CSF. Taken together, these data demonstrate that only the intravenous route of administration is effective in inducing tolerance to MBP.

Various modifications may be made to the preferred embodiments without departing from the spirit and scope of the invention as defined in the appended claims.

The embodiment of the invention in which an exclusive property or privilege is claimed are defined as follows:

1. A method of treating multiple sclerosis in a human in need thereof by administering to said human an effective amount of a peptide consisting of 8 to 25 continuous amino acid residues within residues 61-106 of human myelin basic protein (MBP), wherein human MBP has the sequence of SEQ ID NO:1; wherein said peptide is capable of neutralizing anti-myelin basic protein antibody.

2. The method according to claim 1, wherein the peptide is administered intravenously, intrathecally or a combination of both.

3. The method of claim 2, wherein the peptide is administered at a dose ranging from 1 mg/kg of body weight to 10 mg/kg of body weight.

4. The method according to claim 1, wherein the peptide is in admixture with a pharmaceutical acceptable carrier.

5. The method according to claim 1, wherein the peptide is synthetic.

6. A method of treating multiple sclerosis in a human in need thereof by administering to said human an effective amount of a peptide consisting of 15 to 21 continuous amino acid residues within residues 61-106 of human myelin basic protein (MBP), wherein human MBP has the sequence of SEQ ID NO:1; wherein said peptide is capable of neutralizing anti-myelin basic protein antibody.

7. The method according to claim 6, wherein the peptide is administered intravenously, intrathecally or a combination of both.

8. The method of claim 6, wherein the peptide is administered at a dose ranging from 1 mg/kg of body weight to 10 mg/kg of body weight.

9. The method according to claim 6, wherein the peptide is in admixture with a pharmaceutical acceptable carrier.

10. The method according to claim 6, wherein the peptide is synthetic.

* * * * *

```
                              SEQUENCE LISTING

<160> NUMBER OF SEQ ID NOS: 14

<210> SEQ ID NO 1
<211> LENGTH: 170
<212> TYPE: PRT
<213> ORGANISM: Homo sapiens
<220> FEATURE:
<221> NAME/KEY: misc_feature
<223> OTHER INFORMATION: Human myelin basic protein

<400> SEQUENCE: 1

Ala Ser Gln Lys Arg Pro Ser Gln Arg His Gly Ser Lys Tyr Leu Ala
1               5                   10                  15

Thr Ala Ser Thr Met Asp His Ala Arg His Gly Phe Leu Pro Arg His
            20                  25                  30

Arg Asp Thr Gly Ile Leu Asp Ser Ile Gly Arg Phe Phe Gly Gly Asp
        35                  40                  45

Arg Gly Ala Pro Lys Arg Gly Ser Gly Lys Asp Ser His His Pro Ala
    50                  55                  60

Arg Thr Ala His Tyr Gly Ser Leu Pro Gln Lys Ser His Gly Arg Thr
65                  70                  75                  80

Gln Asp Glu Asn Pro Val Val His Phe Phe Lys Asn Ile Val Thr Pro
                85                  90                  95

Arg Thr Pro Pro Pro Ser Gln Gly Lys Gly Arg Gly Leu Ser Leu Ser
            100                 105                 110

Arg Phe Ser Trp Gly Ala Glu Gly Gln Arg Pro Gly Phe Gly Tyr Gly
        115                 120                 125

Gly Arg Ala Ser Asp Tyr Lys Ser Ala His Lys Gly Phe Lys Gly Val
    130                 135                 140

Asp Ala Gln Gly Thr Leu Ser Lys Ile Phe Lys Leu Gly Gly Arg Asp
145                 150                 155                 160

Ser Arg Ser Gly Ser Pro Met Ala Arg Arg
                165                 170

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val His Phe Phe Lys Asn Ile
1               5

<210> SEQ ID NO 3
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ser His Gly Arg Thr Gln Asp Glu Asn Pro Val Val His Phe Phe
 1               5                  10                  15

Lys Asn Ile Val Thr
            20

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Arg Thr Ala His Tyr Gly Ser Leu Pro Gln Lys Ser His Gly
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His His Pro Ala Arg Thr Ala His Tyr Gly Ser Leu Pro Gln Lys
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Gly Ser Leu Pro Gln Lys Ser His Gly Arg Thr Gln Asp Glu
 1               5                  10                  15

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Gln Asp Glu Asn Pro Val Val His Phe Phe Lys Asn Ile Val Thr
 1               5                  10                  15

Pro Arg

<210> SEQ ID NO 8
<211> LENGTH: 16
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 8

Lys Asn Ile Val Thr Pro Arg Thr Pro Pro Ser Gln Gly Lys Gly
1               5                   10                  15

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Pro Val Val His Phe Phe Lys Asn Ile
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Val Val His Phe Phe Lys Asn Ile Val
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Val His Phe Phe Lys Asn Ile Val Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val His Phe Phe Lys Asn Ile Val Thr Pro
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Glu Asn Pro Val Val His Phe Phe Lys Asn Ile Val Thr Pro Arg Thr
1               5                   10                  15
```

```
<210> SEQ ID NO 14
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His His Pro Ala Arg Thr Ala His Tyr Gly Ser Leu Pro Gln Lys Ser
  1               5                  10                  15

His Gly Arg Thr Gln Asp Glu Asn Pro Val Val His Phe Phe Lys Asn
                 20                  25                  30

Ile Val Thr Pro Arg Thr Pro Pro Pro Ser Gln Gly Lys Gly
                 35                  40                  45
```